United States Patent
Petro

(10) Patent No.: US 6,491,816 B2
(45) Date of Patent: Dec. 10, 2002

(54) APPARATUS FOR PARALLEL HIGH-PERFORMANCE LIQUID CHROMATOGRAPHY WITH SERIAL INJECTION

(75) Inventor: Miroslav Petro, Santa Clara, CA (US)

(73) Assignee: Symyx Technologies, Inc., Santa Clara, CA (US)

( * ) Notice: Subject to any disclaimer, the term of this patent is extended or adjusted under 35 U.S.C. 154(b) by 0 days.

(21) Appl. No.: 09/956,199

(22) Filed: Sep. 18, 2001

(65) Prior Publication Data

US 2002/0020670 A1 Feb. 21, 2002

Related U.S. Application Data

(60) Division of application No. 09/410,546, filed on Oct. 1, 1999, now Pat. No. 6,296,771, which is a continuation-in-part of application No. 09/285,363, filed on Apr. 2, 1999, now abandoned, and a continuation-in-part of application No. 09/285,393, filed on Apr. 2, 1999, now Pat. No. 6,265,226, and a continuation-in-part of application No. 09/285,333, filed on Apr. 2, 1999, now Pat. No. 6,260,407, and a continuation-in-part of application No. 09/285,335, filed on Apr. 2, 1999, now Pat. No. 6,175,409, and a continuation-in-part of application No. 09/285,392, filed on Apr. 2, 1999, now Pat. No. 6,294,388.

(51) Int. Cl.[7] .................................... B01D 15/08
(52) U.S. Cl. .................... 210/198.2; 210/143; 210/656; 210/659; 73/61.52; 422/70
(58) Field of Search ................ 210/635, 656, 210/659, 143, 198.2; 422/70; 436/161; 73/61.52

(56) References Cited

U.S. PATENT DOCUMENTS

| | | | |
|---|---|---|---|
| 3,458,437 A | 7/1969 | Ouano | 210/31 |
| 4,038,874 A | 8/1977 | Baldin et al. | 73/422 GC |
| 4,444,066 A | 4/1984 | Ogle et al. | 73/863.72 |
| 4,631,687 A | 12/1986 | Kowalski et al. | 364/497 |
| 4,711,764 A | 12/1987 | Good | 422/65 |
| 4,816,226 A | 3/1989 | Jordan et al. | 422/81 |
| 4,926,702 A | 5/1990 | Stephens et al. | 73/864.83 |

(List continued on next page.)

FOREIGN PATENT DOCUMENTS

| | | | | |
|---|---|---|---|---|
| DE | 27 31 052 | 1/1979 | | 210/656 |
| DE | 196 41 210 | 4/1998 | | 210/198.2 |
| DE | 197 04 477 | 8/1998 | | 210/198.2 |
| GB | 2 290 283 | 12/1995 | | 210/198.2 |
| JP | 60 115854 | 6/1985 | | 210/656 |
| WO | WO 98/13118 | 4/1998 | | 210/198.2 |

OTHER PUBLICATIONS

Gilson advertisement for Multiple Probe 215 with 889 Injection Module 1 Page Undated.

Jansen, H., et al., "Parallel Column Ion Exchange for Post–Separation pH Modification in Liquid Chromatography," *Journal of Chromatography*, vol. 366, pp. 135–144, (1986).

(List continued on next page.)

*Primary Examiner*—Ernest G. Therkorn

(57) ABSTRACT

High-performance liquid chromatography (HPLC) methods and systems are disclosed that combine sequential, serial injection of a plurality of samples into mobile-phases supplied in parallel to two or more chromatographic columns, such that staggered, parallel separation of the plurality of samples is effected. Because injection of samples is relatively fast as compared to separation, substantial efficiencies are gained with respect to overall sample throughput. The disclosed HPLC methods and systems are preferably applied in connection with combinatorial chemistry, combinatorial material science and more particularly, combinatorial synthesis and screening of polymeric materials.

6 Claims, 11 Drawing Sheets

U.S. PATENT DOCUMENTS

| | | | |
|---|---|---|---|
| 4,980,130 A | 12/1990 | Metzger et al. | 422/70 |
| 4,999,439 A | 3/1991 | Sprecker et al. | 549/397 |
| 5,049,509 A | 9/1991 | Szakasits et al. | 436/140 |
| 5,071,547 A | 12/1991 | Cazer et al. | 210/198.2 |
| 5,106,756 A | 4/1992 | Zaromb | 436/161 |
| 5,108,928 A | 4/1992 | Menard et al. | 436/43 |
| 5,205,845 A | 4/1993 | Sacks et al. | 55/197 |
| 5,240,604 A | 8/1993 | Cortes et al. | 210/198.2 |
| 5,277,871 A | 1/1994 | Fujii et al. | 422/70 |
| 5,443,791 A | 8/1995 | Cathcart et al. | 422/65 |
| 5,474,744 A | 12/1995 | Lerch | 422/100 |
| 5,492,831 A | 2/1996 | Ranger | 436/50 |
| 5,574,216 A | 11/1996 | Hiyama | 73/65.01 |
| 5,603,899 A | 2/1997 | Franciskovich et al. | 422/100 |
| 5,670,054 A * | 9/1997 | Kibbey | 210/656 |
| 5,711,786 A | 1/1998 | Hinshaw | 95/82 |
| 5,766,481 A | 6/1998 | Zambias et al. | 210/656 |
| 5,772,874 A | 6/1998 | Quinn et al. | 210/198.2 |
| 5,783,450 A | 7/1998 | Yoshida et al. | 436/161 |
| 5,814,742 A | 9/1998 | Vissers et al. | 73/863.73 |
| 5,900,934 A | 5/1999 | Gilby et al. | 356/344 |
| 5,918,273 A | 6/1999 | Horn | 73/61.55 |
| 5,919,368 A | 7/1999 | Quinn et al. | 210/635 |
| 5,938,932 A | 8/1999 | Connelly et al. | 210/659 |
| 5,942,433 A | 8/1999 | Parce et al. | 436/514 |
| 6,040,186 A | 3/2000 | Lewis et al. | 436/53 |
| 6,054,047 A | 4/2000 | Hindsgaul et al. | 210/198.2 |
| 6,080,318 A * | 6/2000 | Gumm | 210/198.2 |
| 6,197,198 B1 * | 3/2001 | Messinger | 210/198.2 |
| 6,210,571 B1 * | 4/2001 | Zambias | 210/198.2 |

OTHER PUBLICATIONS

Zeng, Lu., et al., "Developements of a Fully Automated Parallel HPLD/Mass Spectrometry System for the Analytical Characterization and Preparative Purification of Combinatorial Libraries," *Anal. Chem.*, vol. 70, pp. 4380–4388, (1998).

Scholten et al., (1981) J. Chromatography 218: 3–13 "A Fluorescence Detection Of Chloroanilines in Liquid Chromatography Using a Post Column Reaction with Fluorescamine".

* cited by examiner

APPARATUS FOR PARALLEL HIGH-PERFORMANCE LIQUID CHROMATOGRAPHY WITH SERIAL INJECTION

This application is a divisional of U.S. patent application Ser. No. 09/410,546 entitled "Parallel High-Performance Liquid Chromatography with Serial Injection", filed Oct. 1, 1999, now allowed as U.S. Pat. No. 6,296,771, which is itself a continuation-in-part of, and claims priority to the following U.S. patent applications, each of which is hereby incorporated by reference for all purposes: Ser. No. 09/285,363 entitled "Rapid Characterization of Polymers", filed Apr. 2, 1999 by Petro et al., now abandoned in favor of Ser. No. 09/710,801; Ser. No. 09/285,393 entitled "Automated Sampling Methods for Rapid Characterization of Polymers", filed Apr. 2, 1999 by Petro et al., now U.S. Pat. No. 6,265,226; Ser. No. 09/285,333 entitled "High-Temperature Characterization of Polymers", filed Apr. 2, 1999 by Petro et al., now U.S. Pat. No. 6,260,407; Ser. No. 09/285,335 entitled "Flow-Injection Analysis and Variable-Flow Light Scattering Apparatus and Methods for Characterizing Polymers", filed Apr. 2, 1999 by Nielsen et al., now U.S. Pat. No. 6,175,409; and Ser. No. 09/285,392 entitled "Indirect Calibration of Polymer Characterization Systems", filed April 2, 1999 now U.S. Pat. No. 6,294,388 by Petro et al. This application is related to U.S. patent application Ser. No. 09/670,503 entitled "Parallel High-Performance Liquid Chromatography With Post-Separation Treatment" filed Sep. 16, 2000 by Petro et al., which claims the priority benefit of Ser. No. 60/157,338 entitled "Parallel High-Performance Liquid Chromatography With Post-Separation Treatment" filed Oct. 1, 1999 by Petro et al., and is hereby incorporated by reference for all purposes.

BACKGROUND OF INVENTION

The present invention generally relates to liquid chromatography, and specifically, to high-pressure liquid chromatography (HPLC) methods and systems for rapidly separating and/or characterizing a plurality of samples. The invention particularly relates, in a preferred embodiment, to hybrid parallel-serial HPLC methods and systems for separating and/or characterizing a combinatorial library comprising different polymers.

Liquid chromatography is generally well known in the art. High-pressure liquid chromatographic techniques involve injection of a sample into a mobile-phase that flows through a chromatographic column, separation of one or more components of the sample from other components thereof in the chromatographic column, and detection of the separated components with a flow-through detector. Approaches for liquid chromatography typically vary, however, with respect to the basis of separation and with respect to the basis of detection.

Gel permeation chromatography (GPC), a well-known form of size exclusion chromatography (SEC), is a frequently-employed chromatographic technique for separation of samples generally, and for polymer size determination in particular. Another chromatographic separation approach is illustrated by U.S. Pat. No. 5,334,310 to Fréchet et al. and involves the use of a porous monolithic stationary-phase as a separation medium within the chromatographic column, combined with a mobile-phase composition gradient. Other separation approaches are also known in the art, including for example, normal-phase (e.g., adsorption) chromatography and reverse-phase chromatography, hydrophobic interaction chromatography, hydrophilic interaction chromatography, ion-exchange chromatography, affinity chromatography, among others.

After separation, a detector can measure a property of the sample or of a sample component—from which one or more characterizing properties, such as molecular weight can be determined as a function of time. Specifically for polymers, for example, a number of molecular-weight related parameters can be determined, including for example: the weight-average molecular weight ($M_W$), the number-average molecular weight ($M_n$), the molecular-weight distribution shape, and an index of the breadth of the molecular-weight distribution ($M_W/M_n$), known as the polydispersity index (PDI). Other characterizing properties, such as concentration, size (e.g. for particles or polymers), architecture, chemical composition and/or chemical composition distribution can likewise be determined. A variety of continuous-flow detectors have been used for measurements in liquid chromatography systems. Common flow-through detectors include optical detectors such as a differential refractive index detector (RI), an ultraviolet-visible absorbance detector (UV-VIS), or an evaporative mass detector (EMD)—sometimes referred to as an evaporative light scattering detector (ELSD). Additional detection instruments, such as a static-light-scattering detector (SLS), a dynamic-light-scattering detector (DLS), and/or a capillary-viscometric detector (C/V) are likewise known for measurement of properties of interest.

Broadly available liquid chromatography systems are not entirely satisfactory for efficiently screening larger numbers of samples. With respect to polymers, for example, high-performance liquid chromatographic techniques can typically take up to an hour for each sample to ensure a high degree of separation over the wide range of possible molecular weights (i.e., hydrodynamic volumes) for a sample. Notably, however, substantial improvements in sample throughput have been achieved in the art. For example, rapid-serial approaches for characterizing polymers have been developed by Symyx Technologies, Inc. (Santa Clara, Calif.) and disclosed in the aforementioned co-pending U.S. patent applications from which the present application claims priority. As another example, U.S. Pat. No. 5,783,450 to Yoshida et al. discloses rapid-serial protocols and systems for preparation, purification and separation of small molecules such as catecholamines and protaglandins from biological samples such as blood.

Parallel approaches for liquid chromatography have also been contemplated in the art. Zeng et al., *Development of a Fully Automated Parallel HPLC/Mass Spectrometry System for the Analytical Characterization and Preparative Purification of Combinatorial Libraries, Anal. Chem.* 70, 4380–4388 (1998), disclose analytical and preparative HPLC methods and systems involving the sequential pre-loading of samples onto two chromatographic columns, and then applying a mobile-phase in parallel to each of the columns to effect parallel separation of the samples. According to an alternative approach disclosed in U.S. Pat. No. 5,766,481 to Zambias et al., parallel separation of a plurality of molecules is effected by forming a mixture of selected, compatible molecules, and subsequently resolving the mixture sample into its component molecules by separation in a single-channel HPLC system. Parallel approaches have likewise been employed in other separation protocols, such as capillary electrophoresis. See, for example, U.S. Pat. No. 5,900,934 to Gilby et al.

Although such parallel approaches and systems have been generally contemplated, there nonetheless exists a need in the art for improving such approaches and systems with respect to overall sample throughput and/or quality of data. Moreover, with the development of combinatorial materials science techniques that allow for the parallel synthesis of libraries comprising a vast number of diverse industrially relevant materials, and especially polymeric materials, there is a need for HPLC methods and systems to rapidly characterize the properties of samples from such combinatorial libraries.

SUMMARY OF INVENTION

It is therefore an object of the present invention to provide HPLC systems and protocols having a higher overall sample throughput, and in preferred applications, employing such systems and protocols for characterizing combinatorial libraries of material samples such as polymer samples, and particularly, libraries of or derived from reaction mixtures such as polymerization product mixtures, to facilitate the discovery of commercially important materials such as polymeric materials, catalysts, polymerization conditions and/or post-synthesis processing conditions.

Briefly, therefore, the present invention is directed to methods for separating and characterizing components of a plurality of samples with a high-performance liquid chromatography system. According to one preferred method, a mobile phase is supplied (e.g., pumped) in parallel through each of first and second chromatographic columns of a liquid chromatography system. First and second samples are serially injected into the mobile phase of the first and second chromatographic columns, respectively. At least one sample component of the injected first and second samples is then separated from other sample components thereof in the respective chromatographic columns. Preferably, in applications to analytical chromatography, a property of at least one of the separated sample components of the first and second samples is detected. A property of interest can then be determined from the detected property (e.g., by correlation to known standards for the property of interest).

The invention is also directed to several preferred variations of the aforedesribed method. In one preferred variation, four or more different samples are serially and distributively injected into a mobile phase being supplied in parallel to four or more chromatography columns. In another preferred variation of such method, ten or more different samples are serially loaded into an injection system (and preferably into an injector such as an injection valve), and then serially and distributively injected through a multi-port switching valve into one of the mobile phases being supplied in parallel to four or more chromatography columns. In each of the aforementioned methods, the number of parallel chromatographic channels is preferably at least four of more, and the number of samples (e.g., polymer samples) is preferably at least ten or more (and in some cases forty or more). In particular, for polymer screening, the invention is advantageously combined with rapid serial approaches applied in one or more of the parallel chromatographic channels.

The invention is directed as well to a liquid chromatography system useful for rapid separation and/or characterization of a plurality of samples. The system includes two or more chromatographic columns, and two or more supply conduits for providing parallel fluid communication between a liquid mobile-phase source and the two or more chromatographic columns, respectively. The liquid chromatography system also includes an injection system for serially and distributively injecting a plurality of samples into a liquid mobile phase supplied to the two or more chromatographic columns. The injection system comprises an injector and a multi-port switching valve. The injector has a sample-loading port (e.g., an injection port) for receiving a plurality of samples, and has a sample-discharge port for discharging the plurality of samples under pressure to the switching valve. The injector is preferably a multi-loop injection valve of the type known in the art. The switching valve has an inlet port and two or more selectable outlet ports. The inlet port of the switching valve is in fluid communication with the sample-discharge port of the injector, and is in selectable fluid communication with the two or more selectable outlet ports. The two or more selectable outlet ports are themselves in fluid communication with the two or more chromatographic columns, respectively, such that the injection system can serially and distributively inject the plurality of samples into the parallel-supplied mobile phase of the two or more chromatographic columns. A control system is preferably used to control the switching valve—that is, to control which of the two or more selectable outlet ports are in fluid communication with the inlet port. The system can also include one or more detectors having a flow cell in fluid communication with the chromatographic column effluent—for detecting a property of the plurality of samples or sample components. The system can also include an autosampler for loading the samples into the loading port/injection port of the injector.

In preferred embodiments, the system is a high-performance liquid chromatography system comprising four or more chromatographic columns, or eight or more chromatographic columns configured in parallel with respect to the mobile-phase flow through the columns. The system also preferably includes one or more microprocessors and one or more associated control systems or sub-systems for controlling the autosampler, injector, multi-port switching valve, and detectors, as well as the one or more pumps that supply the mobile-phase to the chromatographic columns.

Another aspect of the invention is directed to other applications of the aforementioned methods and systems for evaluating interactions between a plurality of liquid samples (e.g., samples dissolved in, dispersed in or emulsified in a liquid phase) and one or more solid materials or supported materials. Inverse chromatography with the single-injection/parallel mobile phase system is exemplary. More generally, however, the methods and systems of the invention can be applied to study solid/liquid interactions without regard to whether or not separation is effected.

The present invention provides substantial advantages over known approaches for parallel liquid chromatography systems. High overall throughput is achieved with a HPLC system involving time-based resolution of sample components without compromising data quality. In particular, the present invention overcomes limitations associated with the system disclosed by Zeng et al.—involving sequential preloading of the sample onto two columns, and subsequently initiating mobile-phase flow in parallel through the columns to effect parallel separation. Comparatively, the instant methods and system are more accurate and reproducible, since the methods and systems of Zeng et al.—inherently require an equilibration period once mobile-phase flow is initiated. Moreover, the instant methods and systems can be used with a broader range of detectors—especially detectors that would be sensitive to or incompatible with the variation in mobile-phase flow (e.g., evaporative light scattering detectors (ELSD)), as well as with a broader range of rapid-serial techniques, such as overlaid injection, that require or advantageously employ continuous mobile-phase flow. Additionally, the prior art methods are inherently limited with respect to sample throughput. The time spent for stop-flow loading of samples onto or into the columns cannot, a priori, be used for separation, and as such, adversely affects the speed and overall throughput. Moreover, the interruption of flow cannot occur while the preceding sample is resident in the detector (e.g., in the flow cell) without adversely affecting the detector output for that sample. The systems of the instant invention are also comparatively more robust, since the chromatographic columns of the invention are not necessarily subjected to repeated mechanical stresses associated with stopping and initiating the mobile-phase flow.

Other features, objects and advantages of the present invention will be in part apparent to those skilled in art and in part pointed out hereinafter. All references cited in the instant specification are incorporated by reference for all purposes. Moreover, as the patent and non-patent literature relating to the subject matter disclosed and/or claimed herein is substantial, many relevant references are available to a skilled artisan that will provide further instruction with respect to such subject matter.

DETAILED DESCRIPTION OF THE INVENTION

Figure 1A:
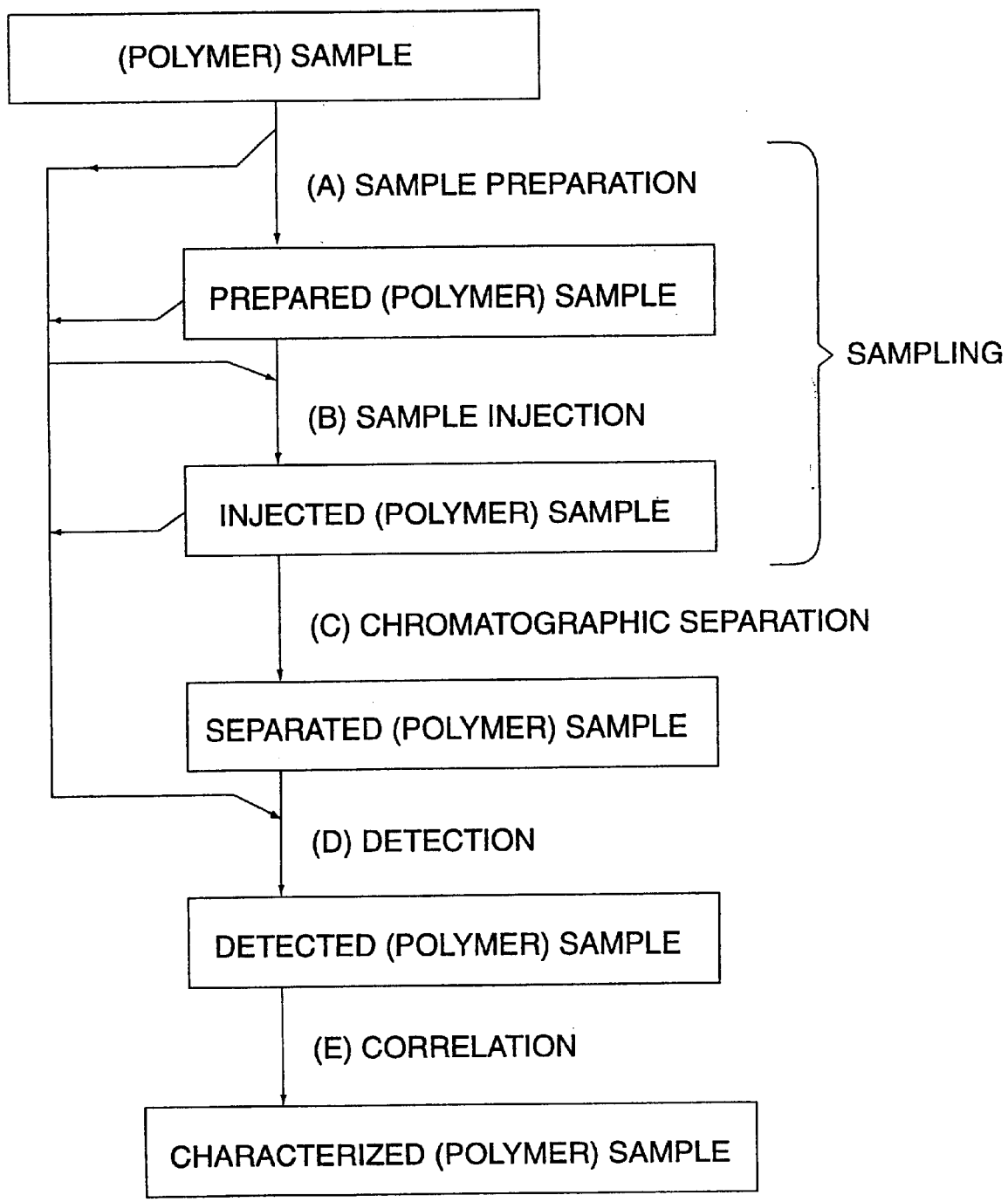
FIG. 1A through FIG. 1D are schematic diagrams showing an overview of polymer characterization process steps (FIG. 1A), and several parallel-serial hybrid protocols for effecting such steps for a plurality of samples ($s_1, s_2, s_3 \ldots s_n$) to obtain corresponding characterizing property information ($p_1, p_2, p_3 \ldots p_n$) (FIG. 1B, FIG. 1C and FIG. 1D).

In the present invention, methods and apparatus having features that enable an effective combinatorial materials research program are provided. Such a research program may be directed, for example, to identifying or optimizing commercially valuable polymers, catalysts or other materials, or to other research goals, such as process characterization and optimization. Other applications, including parallel industrial process monitoring or control are also enabled by the present invention.

Sample characterization approaches and devices of the invention involve hybrid parallel-serial approaches that combine sequential, serial injection of a plurality of samples into mobile-phases supplied in parallel to chromatographic columns, such that staggered, parallel separation of the samples is effected. Specifically, a plurality of samples and/or components thereof are separated and/or characterized by pumping a mobile phase in parallel through each of first and second chromatographic columns of a liquid chromatography system, serially injecting first and second samples into the mobile phase of the first and second chromatographic columns, respectively, separating at least one sample component of the injected first and second samples from other sample components thereof in the respective chromatographic columns, and detecting a property of at least one of the separated sample components of the first and second samples. Because injection of samples is relatively fast as compared to separation, substantial efficiencies are gained with respect to overall throughput. In some preferred approaches and embodiments, the hybrid parallel-series approaches and. systems disclosed herein are combined with rapid-serial protocols, such as those disclosed in the co-pending U.S. patent applications from which the instant application claims priority.

The present invention is preferably applied to, and primarily discussed in connection with combinatorial chemistry, combinatorial material science and more particularly, combinatorial synthesis and screening of polymeric materials. Briefly, in a combinatorial approach for identifying or optimizing materials (e.g. polymers) or reaction conditions, a large compositional space (e.g., of monomers, comonomers, catalysts, catalyst precursors, solvents, initiators, additives, or of relative ratios of two or more of the aforementioned) and/or a large reaction condition space (e.g., of temperature, pressure and reaction time) may be rapidly explored by preparing libraries of diverse materials and then rapidly screening such libraries. Combinatorial polymer libraries can comprise, for example, reaction product mixtures resulting from reactions that are varied with respect to such factors. General aspects of combinatorial approaches for screening a library are discussed in more detail in connection with the above-identified patent applications to which the present invention claims priority. As such, the invention can be applied to combinatorial chemistry and materials science involving polymers and other materials, as well as to more traditional HPLC applications. As such, these and other aspects of the invention described herein are to be considered exemplary and nonlimiting.

Parallel HPLC With Serial Injection

With reference to FIG. 1A, characterizing a sample (e.g. a polymer sample) using an HPLC system can include (A) preparing the sample (e.g., dilution), (B) injecting the sample into a mobile phase of a liquid chromatography system, (C) separating the sample chromatographically, (D) detecting a property of the polymer sample or of a component thereof, and/or (E) correlating the detected property to a characterizing property of interest. As depicted in Figure IA, various characterization protocols may be employed involving some or all of the aforementioned steps. The HPLC methods of the present invention generally include at least the steps of sample injection, chromatographic separation and detection (steps B, C and D).

Figure 1B:
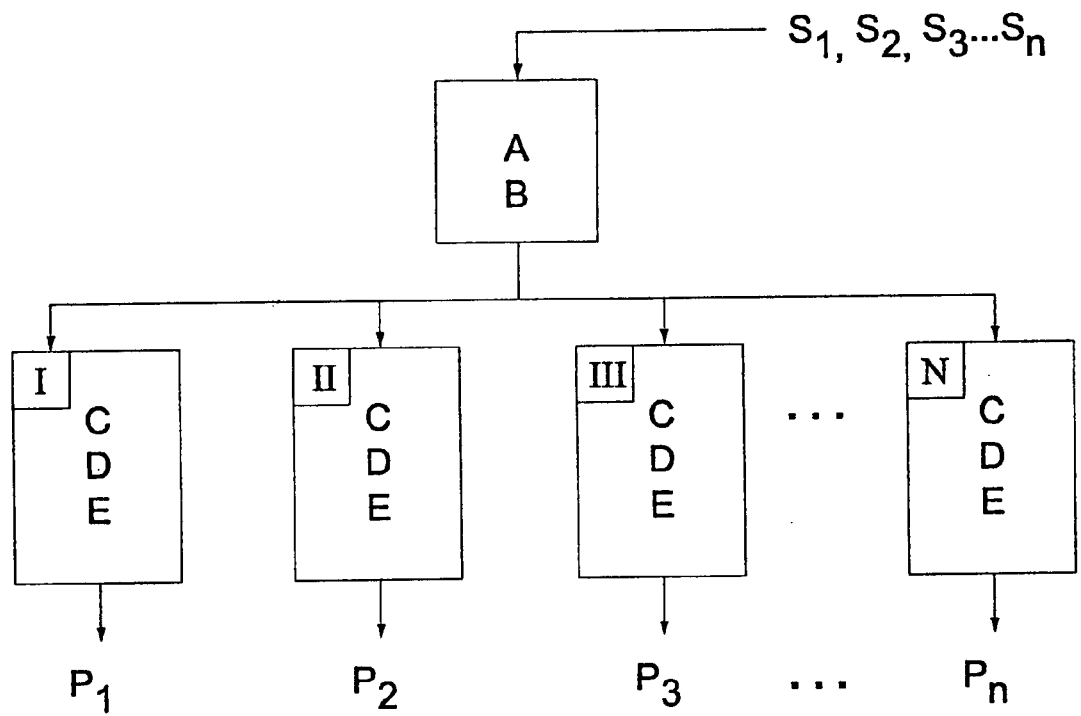
Figure 1C:
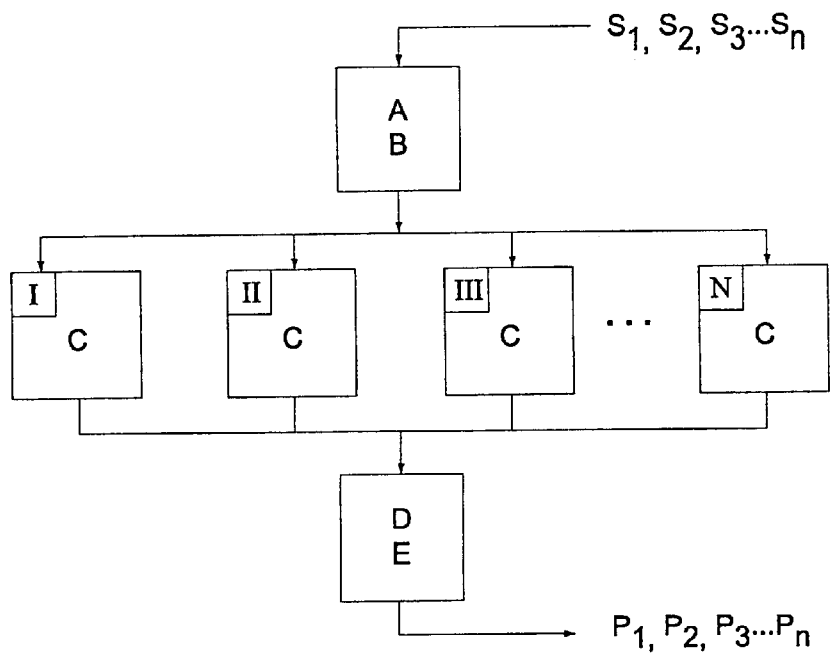

More particularly, the present invention is directed to parallel-hybrid HPLC protocols and systems in which sample injection (step B) is effected in a sequential, rapid-serial manner into mobile-phases supplied in parallel to two or more chromatographic columns, such that separation (step C) of the two or more samples is effected in a staggered (i.e., slightly offset) parallel manner. With reference to FIG. 1B, for example, a plurality of polymer samples ($s_1, s_2, s_3 \ldots s_n$) are prepared and injected in series into the mobile phase of four or more liquid chromatography channels (I, II, III . . . N), and then separated, detected and correlated in a slightly offset (staggered) parallel manner to produce the characterizing property information ($p_1, p_2, p_3 \ldots p_n$) in the same staggered-parallel manner. If each of the separation and detection channels has the same processing rates, then the extent of the parallel offset (or staggering) will be primarily determined by the speed of the serial preparation and injection. In a variation of the preceding example, with reference to FIG. 1C, where the detection and correlation steps are sufficient fast, or where the amount of injection offset is sufficient, a plurality of polymer samples ($s_1, s_2, s_3 \ldots s_n$) can be characterized by serial sample preparation and injection, staggered-parallel chromatographic separation, and then serial detection and correlation, to produce the characterizing property information ($p_1, p_2, p_3 \ldots p_n$) in series. In another embodiment, depicted in FIG. 1D, a plurality of polymer samples ($s_1, s_2, s_3 \ldots s_n$) can be prepared in parallel (step A), serially injected (step B), and then chromatographically separated in a staggered parallel manner (step C), and then detected and correlated in parallel (steps D and E as shown) or in series (not shown) with two or more liquid chromatography channels to produce a parallel stream of corresponding characterizing property information ($p_1, p_2, p_3 \ldots p_n$).

The parallel-hybrid approach discussed above and in greater detail below can be used in combination with one or more of the several rapid-serial optimization approaches—directed toward optimization of one or more characterization steps (e.g., steps (A) through (E) of FIG. 1A) with respect to speed and quality of information—that are disclosed in the above-identified patent applications to which the instant application claims priority.

Figure 2A:
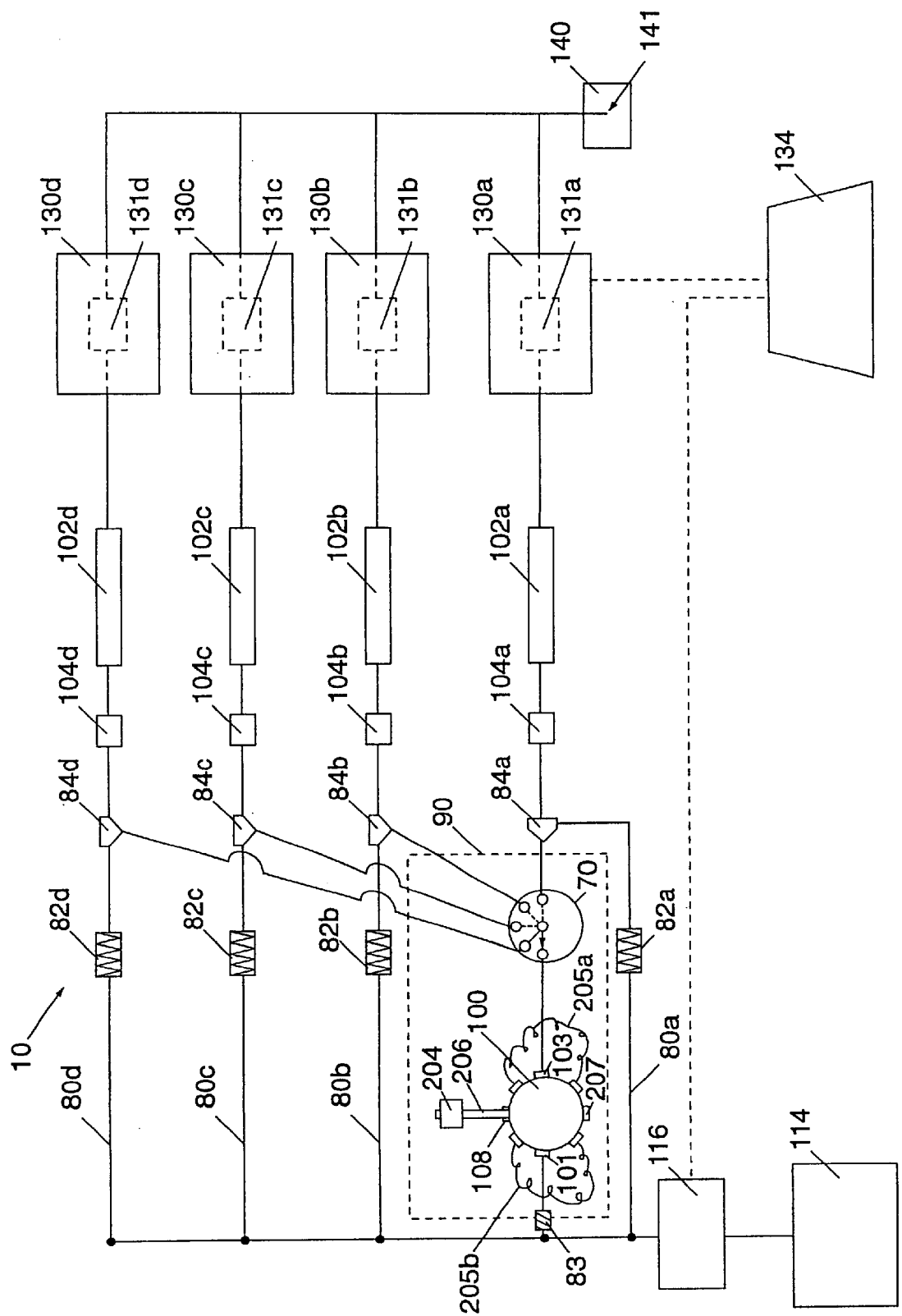
FIG. 2A through FIG. 2C are schematic diagrams illustrating various high-performance liquid chromatography systems as embodiments of the invention.

According to one embodiment, with reference to FIG. 2A, the parallel HPLC system 10 of the present invention comprises a sample injection system 90 for serially and distributively injecting a plurality of samples into a liquid mobile phase supplied in parallel to each of two or more chromatographic columns 102*a*, 102*b*, 102*c*, 102*d*. At least one sample component of the plurality of injected samples are separated from other sample components thereof in the respective chromatographic columns 102*a*, 102*b*, 102*c*, and 102*d*, and a property of at least one of the separated sample components is detected in one or more flow-through detectors 130*a*, 130*b*, 130*c*, 130*d*. Additional details of this embodiment, as well as more general variations of some aspects thereof, are discussed below.

Mobile Phase

Significantly and advantageously, the mobile phase is continuously supplied to the two or more chromatographic columns, and the samples are injected into the mobile phase. This approach is advantageous over an alternative approach in which the mobile phase is intermittently stopped during loading of the sample onto the column. Specifically, this approach provides higher overall sample throughput and ensures the maintenance of equilibrium flow conditions through the chromatographic columns, and as such, improves accuracy, reproducibility and system robustness.

With reference to FIG. 2A, for example, the liquid mobile phase is supplied in parallel to the chromatographic columns 102*a*, 102*b*, 102*c*, 102*d* from a mobile-phase source through two or more column supply conduits 80*a*, 80*b*, 80*c*, 80*d*. After passing through the chromatographic columns 102*a*, 102*b*, 102*c*, 102*d* and detectors 130*a*, 130*b*, 130*c*, 130*d*, the mobile phase is discharged from the system via a common discharge header and effluent port 141 into a waste collection container 140. Alternatively, two or more waste collection containers could be used to receive the mobile phase streams in various shared or dedicated configurations.

Figure 2B:
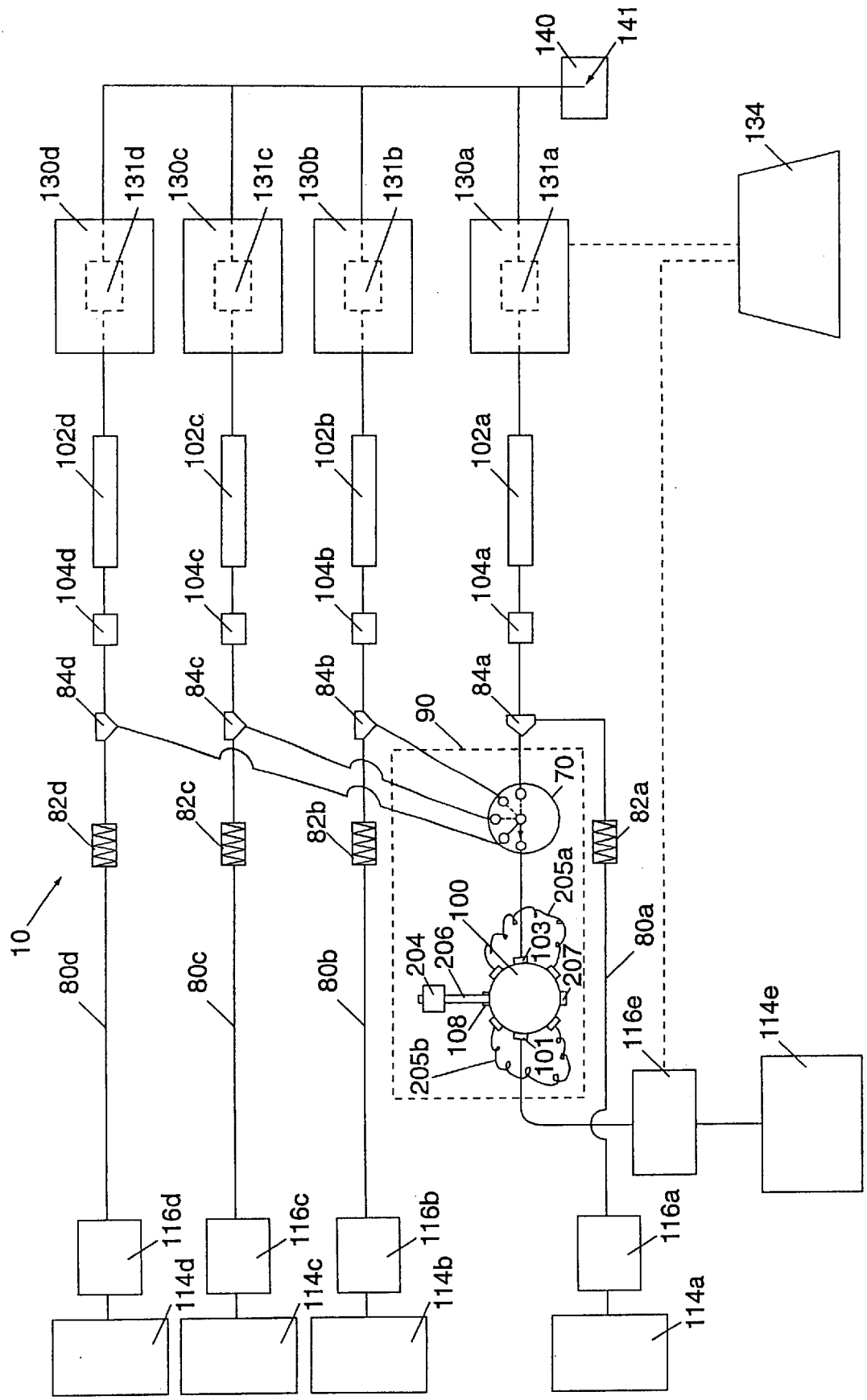
Figure 2C:
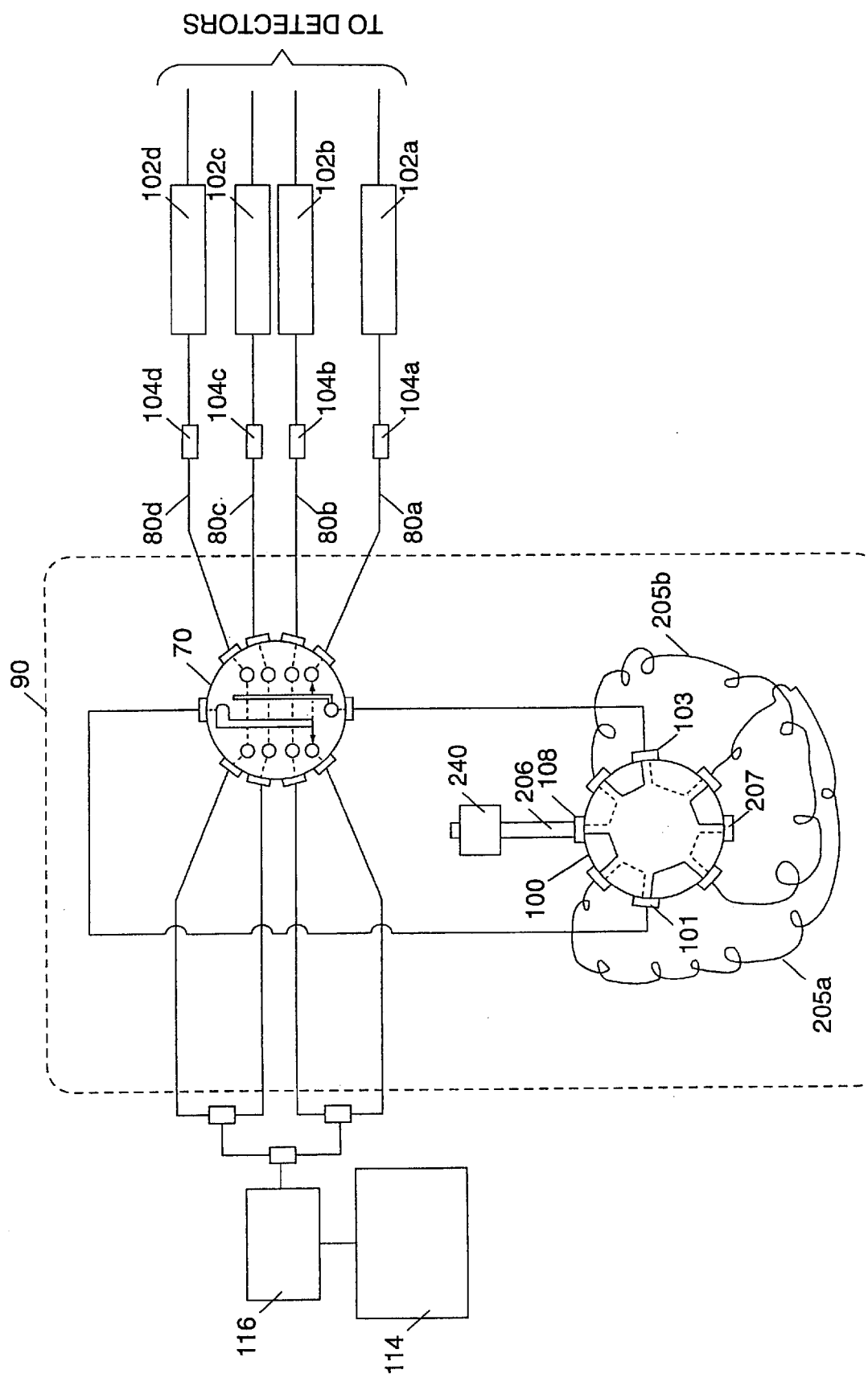

The mobile-phase source can include a single reservoir 114 and a single HPLC pump 116 with appropriate conduit configurations (FIG. 2A, FIG. 2C), or alternatively, can include two or more reservoirs 114*a*, 114*b*, 114*c*, 114*d* and/or two or more HPLC pumps 116*a*, 116*b*, 116*c*, 116*d* with appropriate conduit configurations (FIG. 2B). The mobile-phase source employed in connection with the columns can be the same as (and common to) or different from (and independent of) the mobile-phase source for the injection system, as shown in FIGS. 2A and 2B, respectively. The column supply conduits 80*a*, 80*b*, 80*c*, 80*d* can also include in-line pressure reducers 82*a*, 82*b*, 82*c*, 82*d* (e.g., flow restrictors), respectively, and in-line injection connectors 84*a*, 84*b*, 84*c*, 84*d*, respectively. The resistance provided by the flow-restrictors 82 in each of the supply conduits 80 can be tuned to help minimize flow and pressure fluctuations during and between injections. In particular, the flow restriction in the injection system (e.g., in the flow path during injection) can be controlled, for example with a flow-restrictor 83, to be higher than the flow restriction in the mobile phase supply conduits 80, thereby helping to minimize flow fluctuation. This approach may be limited by the extent of dilution of the sample plug that is acceptable in any particular case. For the system configured as depicted in FIG. 2A, the in-line pressure reducers 82*a* et seq. ensure that the mobile-phase pressure at the injection connectors 84*a* is lower than the injection pressure. The flow or pressure resistance can also be controlled by other means known in the art (e.g., adjustable flow-control valves). Advantageously, such adjustable control means can be used in combination with a pressure-detectors for a comprehensive flow and pressure control system to manage flow/pressure fluctuations. The reservoir(s) 114 can be of any suitable design and capacity, and typically have a volume of about 4 liters. The one or more pumps 116 can be of any type and size suitable to provide a motive force for the mobile-phase fluid through the systems 10. In operation, pump pressures can vary substantially depending on the particular configuration of the system 10, including for example the number of chromatographic columns 102, the separation media employed therein, the desired flowrates, the desired robustness, etc. Internal system pressures (e.g., mobile-phase pressures) delivered by the pump are typically at least about 100 psig, at least about 200 psig, at least about 500 psig or at least about 1000 psig. Higher pressures, up to several thousand psig, can also be employed in robust systems. Hence, the pump pressures can range from about 100 psig to about 6000 psig, from about 200 psig to about 4000 psig, from about 500 psig to about 4000 psig, and from about 1000 psig to about 4000 psig. Typical high-pressure liquid chromatography pumps, available commercially from various sources, such as Waters Model No. 515 (Milford, Mass.) can be employed. The one or more pumps 116 can be controlled with one or more microprocessors 134.

The particular mobile-phase fluid to be included in the reservoir 114 for the flow characterization system can be selected in view of the polymer sample, separation media, separation protocol, detector, detection protocol, desired flowrates, and type of liquid chromatography system. Exemplary mobile-phase fluids for liquid chromatography systems (e.g., GPC, precipitation-redissolution chromatography, adsorption chromatography and reverse-phase chromatography) and for flow-injection analysis systems are discussed below in connection with the column and/or detection protocols. The liquid mobile phase supplied in parallel to each of two or more columns can be the same or different for each of the columns with respect to composition and/or temperature, and moreover can vary for one or more of the columns over time with respect to composition and/or temperature (e.g., as a composition or temperature gradient. Additional reservoirs 114 and additional pumps 116, together with appropriate conduit configurations, can be provided as required to provide such mobile-phase composition gradient or mobile-phase temperature gradient.

Injection System

The injection system comprises an injector and a multi-port switching valve. The injector provides a motive force for injecting a sample under pressure through the multi-port switching valve into the mobile phases being supplied to the two or more chromatographic columns. The multi-port switching valves provides sequential distribution of the samples to the mobile phases of the various columns. The injector and multi-port switching valve can be separate components linked in series by a conduit (e.g., FIG. 2A, FIG. 2B), can be separate components interfacing at the multi-port switching valve (e.g., FIG. 2C) or can be integrated into a single component In a preferred embodiment, shown in FIGS. 2A, 2B and 2C, the injector can be an injection valve 100 such as are typically employed in single-channel HPLC systems. Specifically, the injection valve 100 comprises one or more injection ports 108, one or more sample loops 205a, 205b, one or more mobile-phase inlet ports 101, and one or more mobile-phase outlet ports 103. The sample can be injected directly through an injection port 108 into the mobile phase flowing through the injection valve 100. In preferred embodiments, however, the sample is loaded into the injection valve 100 through a loading port 204 and transfer line 206. In general, a port through which a sample is loaded into the injection valve—whether on the valve itself, or remote therefrom, is considered to be a sample-loading port. The injection valve preferably has one or more resident sample loops 205a, 205b—typical of those used for a high pressure liquid chromatography system. The injection valve 100 can be a single-loop or multi-loop injection valve. After the sample is loaded into the injection valve 100, the valve 100 is actuated to discharge the sample from a sample-discharge port of the injector, and to deliver the sample under pressure through the multi-port switching valve to the mobile phase of a chromatographic column. The delivery pressure is greater than the pressure of the mobile-phase being supplied to the column.

Figure 3:
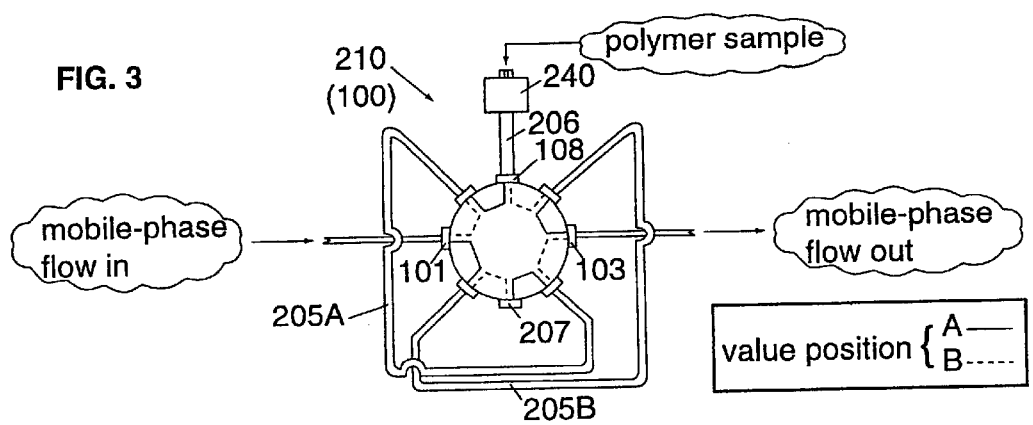
FIG. 3 is a schematic diagram illustrating an eight-port injection valve that can be used (in connection with a multi-port switching valve) for loading a polymer sample and for injection thereof into a mobile phase of a HPLC.

With reference to FIG. 3, the injection valve 100 can be an 8-port, two-loop injection valve 210 (100) that operates as follows. Numerals in parenthesis refer to corresponding parts of the injection valve of FIGS. 2A and 2B. A first sample is loaded directly into an injection port 108 or indirectly through a loading port 204, transfer line 206 and the injection port 108 at relatively low pressure compared to the pressure of the mobile phase. The loading port 204 can be adapted in size to accommodate one or more injection probes (tips) of a manual or an automated sample delivery unit (e.g. an auto-sampler). When the 8-ported valve is in valve position "A" (with internal flow-paths for the valve indicated by solid lines), the first sample is loaded into a sample loop 205A while the mobile phase flows through the valve via mobile-phase inlet port 101 (the flow-in port), sample loop 205B, and mobile-phase outlet port 103 (the flow-out port). The sample loops 205A and 205B can be of equal volume or of varying volume. Optionally, one or more of the loops can be operated as a flow-resistor (and/or replaced with a different type of flow-resistor) or completely plugged, such that no mobile phase flows through the injector between injections. Advantageously, this may help to minimize the flow fluctuations in the mobile phase caused by injection of the samples. A waste port 207 can be employed for receiving any overflow sample and/or for flushing the valve after each sample, if necessary. When the injection valve 210 is switched to the valve "B" position (with internal flow-paths for the valve now indicated by the dashed lines), the mobile phase then flows through the valve via mobile-phase inlet port 100, sample port 205A, and mobile-phase outlet port 103, and the first sample is thereby injected, via the multi-port switching valve, into the mobile phase of one of the chromatographic columns 202 of the liquid chromatography system 10. The mobile-phase outlet port 103 is the sample-discharge port of the injection valve when a sample is present in the mobile phase. While the first sample is being injected from sample loop 205A into the first mobile phase, a second sample can be loaded into sample loop 205B, ready to be injected once the injection valve 100 is switched back to valve position A, and the multi-port switching valve is switched to provide a path of fluid communication to the mobile phase of a second chromatographic column. Eight-ported valves, such as represented in FIG. 3, can be purchased from Valvco Instruments Co. Inc. (Houston, Tex.), and the purchased valve fittings can be modified as described above for use in connection with a flow characterization system. An eight port injection valve 210 is a preferred injection valve 100 because the two sample loops 205A, 205B allow the flow characterization system to be ready for sample loading at all times (i.e., has a load/load capability). While the eight-port valve 210 depicted schematically in FIG. 3 is a preferred configuration, other high-pressure injection valves can also be suitably employed, including, without limitation, valves having a greater or lesser number of ports. Typically, however, a high-pressure injection valve will have from 6 to 24 ports.

While the aforementioned embodiment is preferred, the particular design of the injection valve is not critical. The injection valve 100 (210) can be configured, for example, to have more than one injection port 108, a single injection port 108, and in either case, the single or multiple injection ports 108 be in fluid communication with a number of loading ports 204 via a number of transfer lines 206 in order to receive samples independently from a number of different injection probes, including, for example, a manual injection probes, and one or more probes associated with automated delivery systems, such as one or more robotic auto-samplers. The injection valve can also have a larger number of sample loops with the same or with varying volumes, to accommodate different samples sizes.

The multi-port switching valve can be of various designs and configurations that provide for sequentially receiving a series of samples from the injector, and distributively directing the series of samples to the mobile phases supplied to the various chromatographic columns. Typically, and preferably, with reference to FIG. 4A for example, the multi-port switching valve 70 will have at least one inlet port 72 and two or more selectable outlet ports 74a, 74b, 74c, 74d. The inlet port 72 is in fluid communication with the sample-discharge port of the injector (e.g., port 103 of the injection valve 100 of FIG. 3). The sample inlet port 72 is also in selectable fluid communication with the two or more selectable outlet ports 74a, 74b, 74c, 74d. Switch 76 can be used to selectively connect the inlet port 72 with one of the desired outlet ports 74. The switch 76 can be manually or automatically controlled. The two or more selectable outlet ports 74 are themselves in fluid communication with the two or more chromatographic columns 102, respectively (typically via the two or more column supply conduits). As such, the serially-injected plurality of samples can be serially and distributively injected into the mobile phase of the two or more chromatographic columns. Such multi-port switching valves are commercially available from numerous sources, including for example Valvco, supra. Although the multi-port switching valve is preferably a rotary-type, other configurations are possible and are to be considered as within the scope of the invention.

Multi-port switching valves having selectable outlet ports 74 for use with larger numbers of columns can also be employed. FIG. 4B shows, for example, an analogous multi-part switching valve 70 suitable for use with eight columns 102. To accommodate the serial, distributive delivery of samples to even larger numbers of parallel chromatographic columns 102, nested arrangements of multi-port switching valves can be employed. With reference to FIG. 4C, for example, a plurality of samples can be selectively distributed through a multi-port switching valve 70 to sixty-four (64) columns using a nested arrangement of the 8-outlet port valve of FIG. 4B.

Figure 4A:
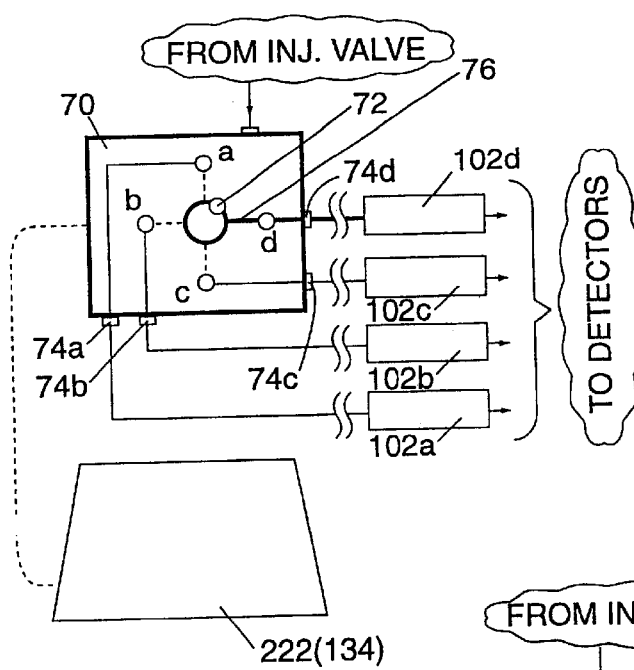
FIG. 4A through FIG. 4C are schematic diagrams illustrating various embodiments of a multi-port switching valve, together with various configurations for fluid communication between the outlet ports of the multi-port switching valve and four chromatographic channels (FIG. 4A), eight chromatographic channels (FIG. 4B) or sixty-four chromatographic channels (FIG. 4C).
Figure 4B:
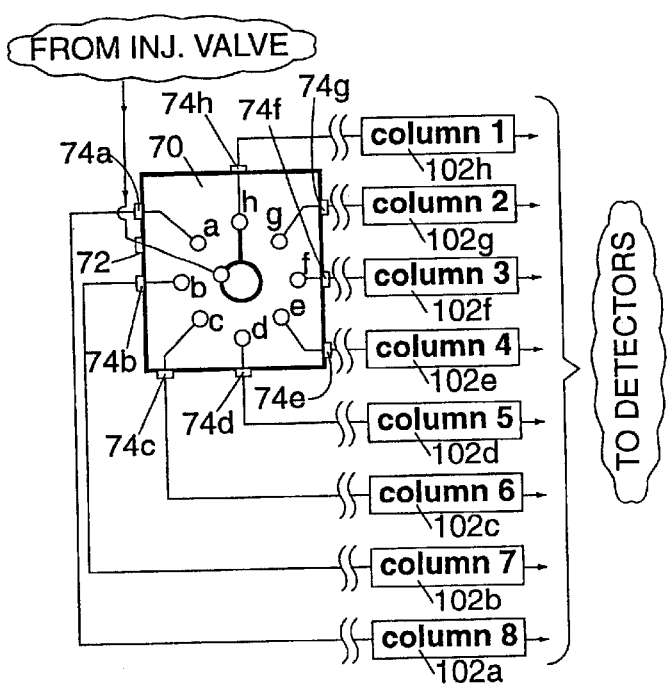
Figure 4C:
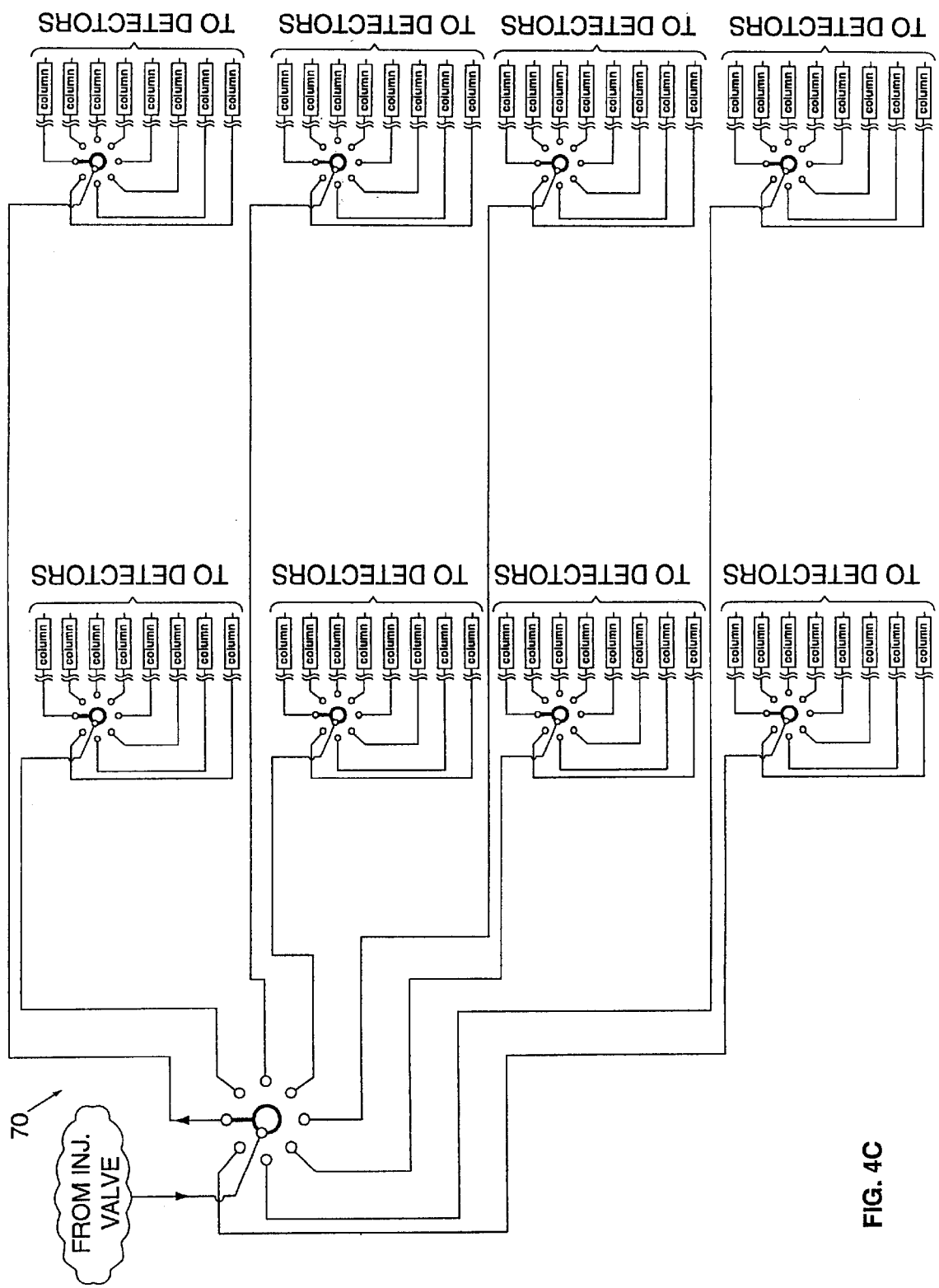

The injector (e.g., injection valve) and/or the multi-port switching valve are preferably controlled using a microprocessor, shown as 222 (134) in FIG. 4A, in combination with a control system. Specifically, referring to FIG. 4A, the control system controls which of the two or more selectable outlet ports 74a, 74b, 74c, 74d of the switching valve 70 are in fluid communication with the inlet port 72 thereof. The control system can comprise, in addition to the microprocessor 222 (134), a control element for actuating switch 76 in electronic communication with the microprocessor. The microprocessor is preferably the same microprocessor as is used for controlling sampling (222 in FIG. 5, discussed below), and can also be the same microprocessor as is used for controlling the HPLC pumps (134 in FIGS. 2A and 2B, discussed above). Particular control schemes (with respect to timing and selection of columns, etc.) are discussed in greater detail below.

Sampling

Sample loading into the injection system, also referred to herein as "sampling", can be effected in any suitable manner, and the particular manner employed is not critical to the invention. Sampling of a sample generally refers to a plurality of steps which include withdrawing a polymer sample from a sample container and delivering at least a portion of the withdrawn sample to the injection system of the HPLC system. Sampling may also include additional steps, particularly and preferably, sample preparation steps. (See FIG. 1A). In one approach, only one sample is withdrawn into the auto-sampler probe at a time and only one sample resides in the probe at one time. The one sample is expelled therefrom (for sample preparation and/or into the polymer characterization system) before drawing the next sample. In an alternative approach, however, two or more samples can be withdrawn into the auto-sampler probe sequentially, spatially separated by a solvent, such that the two or more samples reside in the probe at the same time. Such a "candystriping" approach can provide for very high auto-sampler throughputs for rapid introduction of the one or more samples into the flow characterization system.

The sample container from which the polymer sample is withdrawn is not critical. The sample container can be, for example a sample-containing well. The sample-containing well can be a sample vial, a plurality of sample vials, or a sample-containing well within an array of sample-containing wells (e.g., constituting a polymer sample library). The sample container can alternatively be a sample port from a sample line in fluid communication with an industrial process line, such as a polymerization process line.

In the general case, sampling can be effected manually, in a semi-automatic manner or in an automatic manner. A polymer sample can be withdrawn from a sample container manually, for example, with a pipette or with a syringe-type manual probe, and then manually delivered to a loading port or an injection port of a polymer characterization system. In a semi-automatic protocol, some aspect of the protocol is effected automatically (e.g., delivery), but some other aspect requires manual intervention (e.g., withdrawal of polymer samples from a process control line). Preferably, however, the polymer sample(s) are withdrawn from a sample container and delivered to the characterization system in a fully automated manner—for example, with an auto-sampler.

A plurality of samples, such as those included within a library of samples, is preferably delivered to the injection system (e.g., to injection valve 100 in FIG. 2A) for loading into the HPLC system, with an automatic delivery device, such as an auto-sampler. As used herein, the term "auto-sampler" refers to an apparatus suitable for automated sampling of polymer samples for characterization, including automated withdrawal of a polymer sample from a sample container, and automated loading of at least a portion of the withdrawn sample into an injection port or a loading port of a flow characterization system (e.g. a liquid chromatography system).

Automated sampling equipment is available commercially for introducing multiple samples into liquid flow systems in a serial manner. For example, auto-samplers that can be suitably adapted for use in connection with the present invention for some applications are available from Gilson. However, the applicablity of such commercially-available auto-sampling equipment is limited with respect to the required speed of injection. For example, for high-throughput characterization with an eight-channel parallel chromatographic system with serial injection and a sixty-second analysis time, the required serial injection interval would be about 7.5 seconds. For such applications, improved auto-samplers as disclosed in co-pending U.S. patent application Ser. No. 09/285,393 entitled "Automated Sampling Methods for Rapid Characterization of Polymers", filed Apr. 2, 1999 by Petro et al are preferably employed. Such auto-samplers provide high-throughput, with substantial flexibility with respect to sample preparation, etc., and as such, are well suited to applications of the present invention to combinatorial materials science research.

Figure 5:
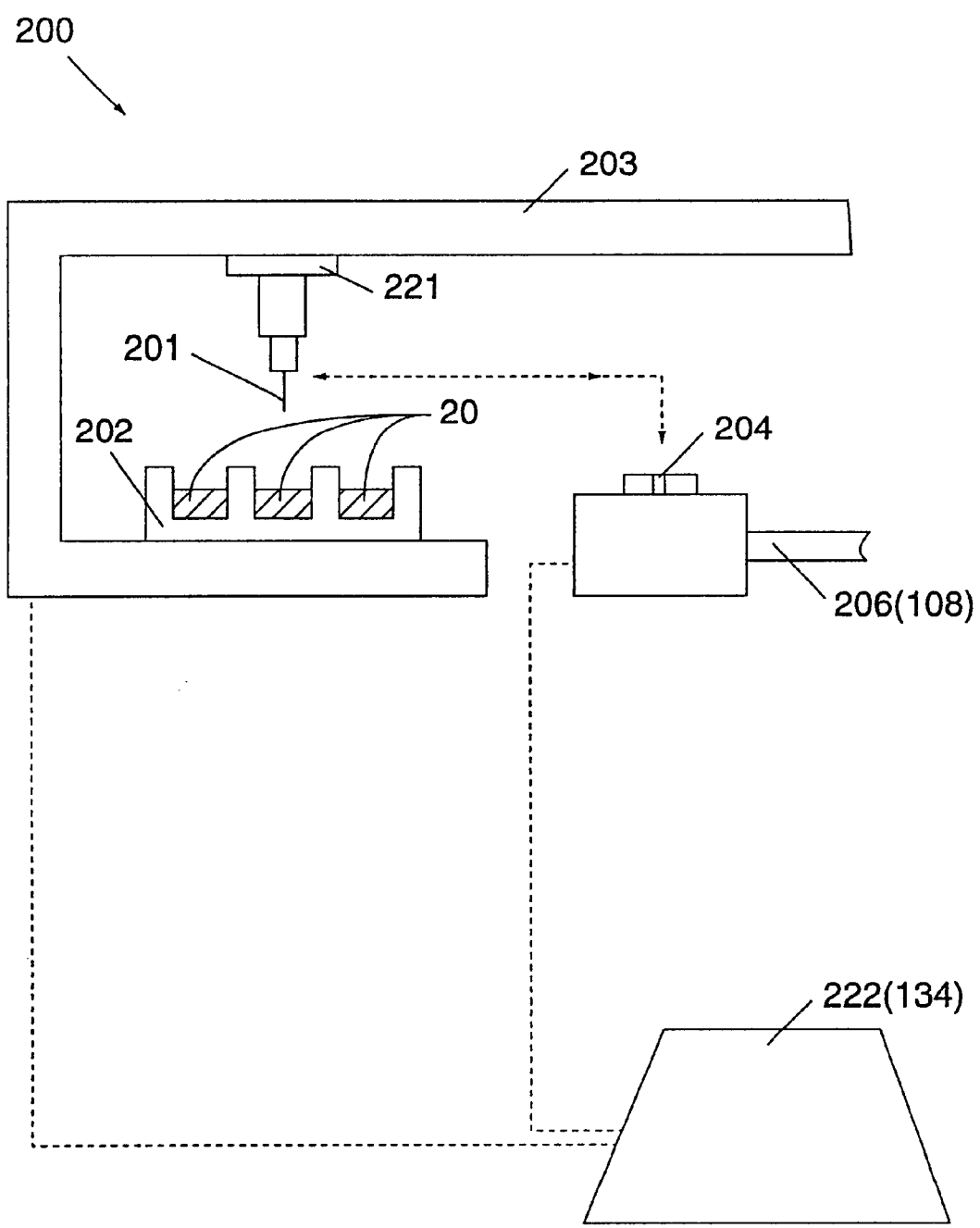
FIG. 5 is a schematic diagram illustrating an automated sampling system.

Briefly, with reference to FIG. 5, in a preferred embodiment an auto-sampler 200 can comprise a movable probe (tip) 201, typically mounted on a support arm 203, a translation station 221 for providing three-dimensional motion of the probe, and a microprocessor 222 for controlling three-dimensional motion of the probe between various spatial addresses. The auto-sampler 200 preferably also comprises a user-interface (not shown) to allow for user programming of the microprocessor 222 with respect to probe motion and manipulations. The probe 201 can have an interior surface defining a sample-cavity and an inlet port for fluid communication between the sample cavity and a polymer sample 20. The probe 201 is also adapted for fluid communication with an injection port 108 (FIG. 2A, FIG. 2B) or a loading port 204 (FIG. 2A, 2B) of the injection system 90. The support arm 203 is preferably an XYZ robotic arm, such as can be commercially obtained from Cavro Scientific Instruments, Inc. (Sunnyvale, Calif.) among others. To improve smoothness of operation at high speeds, such XYZ robotic arms preferably have motions based on gradient variations rather than step-function variations, and preferably are belt-driven rather than shaft driven. The microprocessor 222 can be a computer and can be the same or different from the microprocessor 134 (FIG. 2A, FIG. 2B) used to control the detectors 130 (FIG. 2A, FIG. 2B) and data acquisition therefrom. The auto-sampler can further comprise one or more pumps (not shown), preferably syringe pumps, for drawing and/or expelling liquids, and related connection lines (not shown) for fluid communication between the pumps, the probe 201, and liquid (e.g. solvent) reservoirs. Preferred embodiments include two or more syringe pumps—one with a relatively lower flowrate capacity and one with a relatively higher flowrate capacity. Alternative pump configurations, such as peristaltic pumps, vacuum-pumps or other motive-force providing means can be used additionally or alternatively. Sampling throughputs may also be enhanced by using two or more robotic arms together. It is likewise possible to have more two or more sample probes in connection with a single robotic arm—for example, such as an array of two or more probes each capable of synchronized motion relative to each other.

In operation, the microprocessor 222 of the auto-sampler 200 can be programmed to direct the auto-sampler 200 to withdraw a sample 20 (e.g. a polymer solution comprising a dissolved polymer) from a sample container (e.g., a sample well) formed in a sample tray 202 into the injection probe 201, and subsequently to direct the probe 201 to the loading port 204 for loading the sample into the characterization system through transfer line 206. In preferred embodiments, the auto-sampler can be programmed to automatically sample each well of a library of samples one after the other whereby a plurality of samples are serially loaded into the flow characterization system, and subsequently serially injected into the mobile phase of the characterization system in a plug flow fashion. Preferably, the microprocessor 222 of the auto-sampler comprises a user-interface that can be programmed to allow for variations from a normal sampling routine (e.g., skipping certain elements at certain spatial addresses of a library). The auto-sampler 200 can also be controlled for manual operation on an individual sample by sample basis.

The microprocessor 222 is also preferably user-programmable to accommodate libraries of samples having varying arrangements of arrays of samples (e.g. square arrays with "n-rows" by "n-columns", rectangular arrays with "n-rows" by "m-columns", round arrays, triangular arrays with "r-" by "r-" by "r-" equilateral sides, triangular arrays with "r-base" by "s-" by "s-" isosceles sides, etc., where n, m, r, and s are integers). More particularly, for example, with respect to square or rectangular arrays, a two sets of samples (e.g., libraries) having different spatial configurations can be sampled as follows. First, an auto-sampler is programmed (e.g., via a user interface module) with location information for a first set of samples comprising a plurality of samples in a plurality of sample containers in first spatial arrangement (e.g., "n-rows" by "m-columns", where n and m are integers). The first set of samples are serially withdrawn from their respective sample containers, and at least a portion of each of the withdrawn first set of samples are serially delivered to the sample-loading port of the injection system. The auto-sampler is then reprogrammed with location information for a second set of liquid samples that comprise a plurality of samples in a plurality of sample containers in second spatial arrangement (e.g., "p-rows" by "q-columns", where p and q are integers). The second set of samples are serially withdrawn from their respective sample containers, and at least a portion of each of the withdrawn second set of samples are serially delivered to the sample-loading port of the injection system.

In a preferred protocol for sampling a plurality of samples, an auto-sampler provides for rapid-serial loading of the plurality of polymer samples into a common injection port of an injection valve. More specifically, a plurality of samples is sampled as follows. At a first withdrawal time, $t_{ASW1}$, a first sample is withdrawn from a first sample container at a first location into a probe of an auto-sampler. At least a portion of the withdrawn first sample is then delivered to an injection port of a HPLC system, either directly, or through a loading port and a transfer line. After delivery of the first sample, a second sample is, at a second withdrawal time, $t_{ASW2}$, withdrawn from a second sample container at a second location into the auto-sampler probe. At least a portion of the withdrawn second sample is then delivered (directly or indirectly) to the sample-loading port (e.g., injection port). The cycle can then be repeated, as necessary, in an automated manner, for additional samples included within the plurality of samples.

The auto-sampler cycle time, $T_{AS}$, delineated by the difference in time, $t_{ASW2}-t_{ASW1}$, is not critical, and can vary widely depending on the application of the present invention. If the parallel chromatography techniques of the present invention are applied in connection with standard, conventional HPLC systems and protocols (typically involving from about 30 minutes to about 60 minutes or more per sample), the sampling cycle time, $T_{AS}$, can range from about ten seconds to about 30 minutes or more. If, however, the parallel chromatography techniques of the invention are applied in connection with rapid-serial HPLC systems and protocols as disclosed in the above-identified co-pending applications from which the present application claims priority, (typically involving from about less than 1 minute per sample to about 10 minutes per sample), the sampling cycle time, $T_{AS}$, can range from about ten seconds to about 4 minutes or more. In general, the sampling time, $T_{AS}$, is preferably not more than about 10 seconds, not more than about 15 seconds, not more than about 20 seconds, not more than about 30 seconds, not more than about 1 minute, not more than about 2 minutes, not more than about 4 minutes, not more than about 8 minutes, not more than about 10 minutes, not more than about 20 minutes, or not more than about 30 minutes.

Figure 1D:
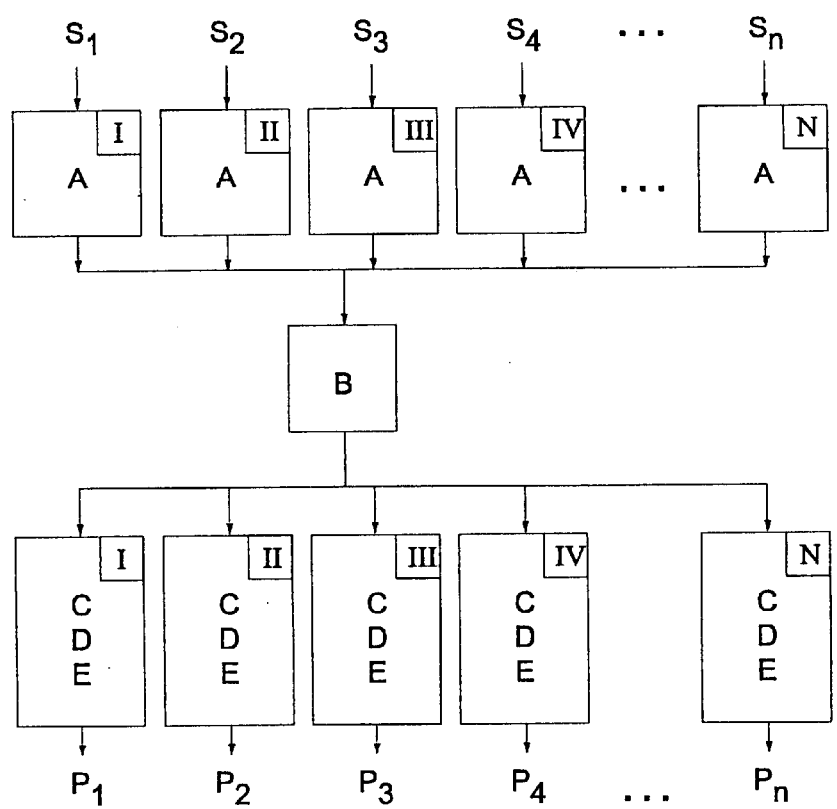

The preferred protocol for sampling a plurality of polymer samples can also include additional automated steps, as described in the above-identified cases from which the present application claims priority. In particular, sample preparation steps can be incorporated into the sampling routine. Such preparation steps can generally be effected in series with the sample loading/injection steps (See, for example, FIGS. 1B and 1C), or alternatively, can be effected in parallel with each other (FIG. 1D).

Sample-Distribution Schemes

Various schemes for the timing of loading, injecting and distributing the serially received samples among the two or more chromatographic columns for separation and subsequent detection can be employed. In general, the selection of a particular scheme can depend on factors such as the number of samples being characterized, the chemical diversity of samples, the number of parallel chromatographic columns in the HPLC system of the invention, the size of the columns, the separation media and separation type (e.g., GPC, precipitation-redissolution, adsorption, etc.), the configuration of the detector(s), and the detection protocols, among others. As such, the schemes disclosed herein are to be considered exemplary and non-limiting.

In the general case, a plurality of samples, preferably four or more different samples, and most preferably ten or more different samples, are serially loaded into an injector, and then serially injected through the multi-port switching valve into the parallel-supplied mobile phase of two or more, and preferably four or more chromatographic columns. The multi-port switching valve is controlled such that the (preferably ten or more) samples are distributively injected into the mobile phase of a first and a second (and preferably also a third and a fourth) of the two or more (and preferably of the four or more) chromatographic columns. At least one sample component of the injected four or more samples is separated from other sample components thereof in the respective chromatographic columns, and a property thereof is subsequently detected. For the purpose of illustration, and without limitation, the following preferred schemes are outlined and discussed in the context of screening ten or more samples with a parallel-serial HPLC system having four chromatographic separation channels (ie., at least four columns).

In a first approach, the sampling can be on a regular, recurring time interval (e.g., every two minutes—assuming 4 columns with an eight minute overall separation/characterization cycle time) such that the injector and the multi-port switching valve receives a sample on the same interval (e.g., once every two minutes). Control of the injector and multi-port switching valve can then be synchronized with each other and with the auto-sampler (with appropriate timing offsets to provide for the sampling, injecting and switching operations, as necessary) and the samples can be regularly distributed to a different chromatography channel on the same time interval (e.g. once every two minutes). The distribution of samples to the various columns by the multiport switching valve can advantageously follow a regular pattern. For example, the switching valve can provide for injection of samples 1, 2, 3, 4, 5, 6, 7, 8, 9 and 10 into the mobile phase of columns 1, 2, 3, 4, 1, 2, 3, 4, 1 and 2, respectively. Because sampling, injection and switching occur relatively fast relative to the separation step, the overall sample throughput for the entire process can be effected based solely on the synchronized time interval—with a dramatic increase in the effective rate of separation (i.e., the actual separation time required (8 minutes) divided by the number of columns (4)—such that once steady-state is reached, the sample throughput for the exemplified case will be one sample every two minutes).

Figure 6:
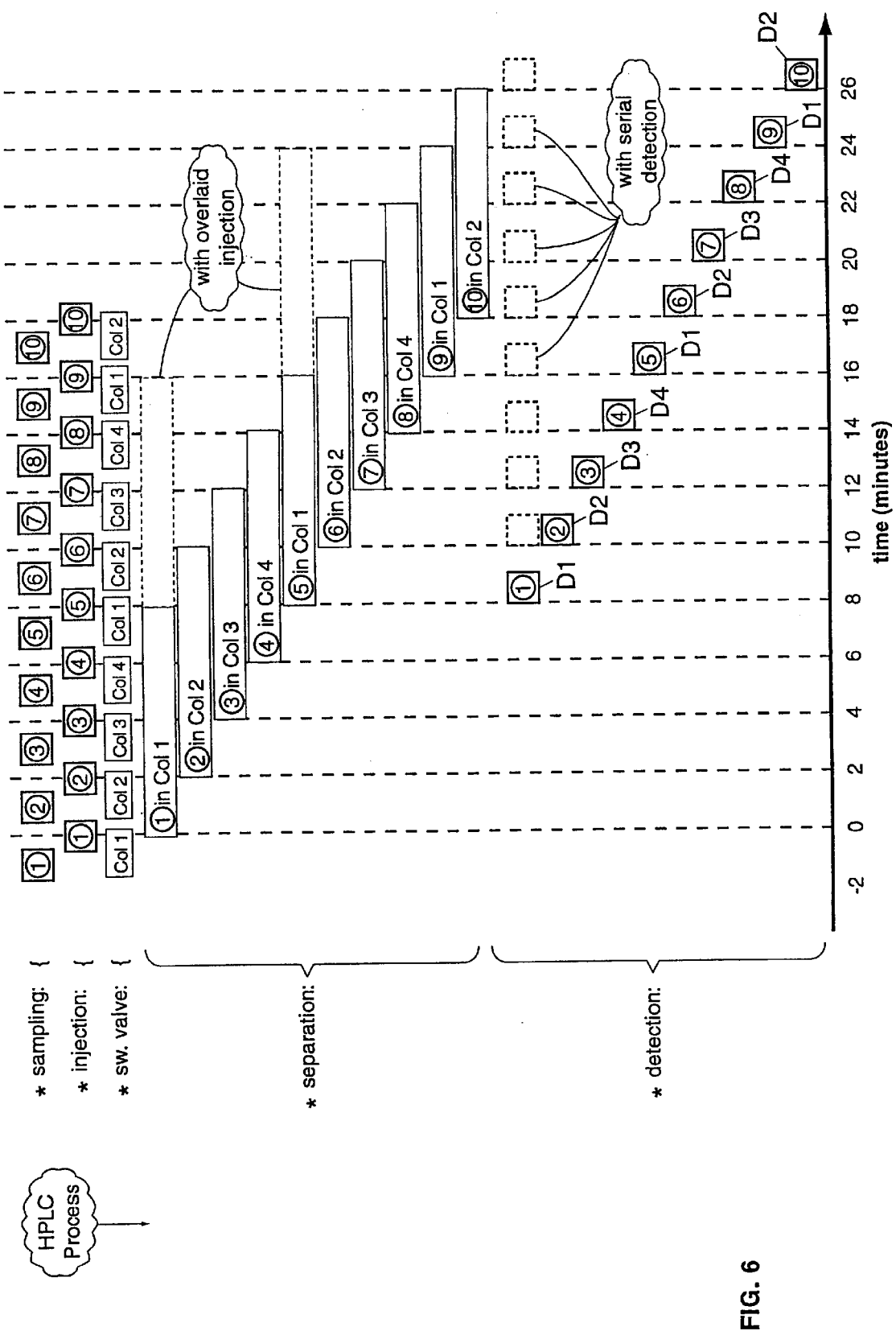
FIG. 6 is a graphical representation illustrating one scheme for serial sampling, and serial, distributive injection of ten samples (indicated as circled numerals—e.g. a circled "1") into a mobile phase supplied in parallel to four chromatographic channels, together with parallel detection with four detectors (indicated as "D1" through "D4"), or with serial detection with a single detector (indicated with dashed-line boxes).

More specifically, with reference to FIG. 6, the multi-port switching valve is controlled such that a first of the ten or more samples (represented as a circled "1") is sampled, and then injected (at t=0) through the multi-port switching valve (selected to Col. 1) into a mobile phase of the first column. A second of the ten or more samples (represented as a circled "2") is then sampled, and the switching valve is selected to Column 2. The second sample is then injected (at t=2 minutes) through the multi-port switching valve into a mobile phase of the second column. A third of the ten or more samples (represented as a circled "3") is then sampled, and the switching valve is selected to Column 3. The third sample is then injected (at t=4 minutes) through the multi-port switching valve into a mobile phase of the third column. A fourth of the ten or more samples (represented as a circled "4") is then sampled, and the switching valve is selected to Column 4. The fourth sample is then injected (at t=6 minutes) through the multi-port switching valve into a mobile phase of the fourth column. A fifth of the ten or more samples (represented as a circled "5") is then sampled, and the switching valve is selected to Column 1. The fifth sample is then injected (at t=8 minutes) through the multi-port switching valve into a mobile phase of the first column. A sixth of the ten or more samples (represented as a circled "6") is then sampled, and the switching valve is selected to Column 2. The sixth sample is then injected (at t=10 minutes) through the multi-port switching valve into a mobile phase of the second column. A seventh of the ten or more samples (represented as a circled "7") is then sampled, and the switching valve is selected to Column 3. The seventh sample is then injected (at t=12 minutes) through the multi-port switching valve into a mobile phase of the third column. An eighth of the ten or more samples (represented as a circled "8") is then sampled, and the switching valve is selected to Column 4. The eighth sample is then injected (at t=14 minutes) through the multi-port switching valve into a mobile phase of the fourth column. A ninth of the ten or more samples (represented as a circled "9") is then sampled, and the switching valve is selected to Column 1. The ninth sample is then injected (at t=16 minutes) through the multi-port switching valve into a mobile phase of the first column. A tenth of the ten or more samples (represented as a circled "10") is then sampled, and the switching valve is selected to Column 2. The sixth sample is then injected (at t=10 minutes) through the multi-port switching valve into a mobile phase of the second column. As shown in FIG. 6, injection to the mobile phase of the four columns is effected in a serial manner, whereas separation in the respective columns is essentially parallel (simultaneous) for at least two or more consecutive samples (although such separation is staggered with respect to its initiation). If more than ten samples are to be characterized, then the sequence can continue in the same such pattern. If more than four parallel chromatographic channels are employed, the distribution pattern can include such the mobile phases of the associated additional columns. Hence, the actual cycle times for switching the multi-port switching valve between various channels, can be the same as that outlined above in connection with the sampling cycle times, $T_{A-S}$, assuming synchronized operation. Of course, independent cycle times, and control thereof, can also be employed, as desired, for synchronous and/or a synchronous operation of the injector and multi-port cycle valve (relative to sampling).

The aforementioned approach, in which the sampler, injector, and multi-port switching valve are all actuated, synchronously or asynchronously, on a regular, recurring time interval is particularly advantageous in connection with applications of the parallel-serial HPLC system of the invention for evaluating combinatorial libraries of materials, such as polymers. In particular, the regular timing and regular pattern can provide for synchronous data collection and processing, and integration with synthesis data. Moreover, the control systems are relatively straightforward. Additionally, such an approach is particularly advantageous and is a particularly preferred embodiment, when it is used in combination with rapid-serial chromatographic separation techniques applied to one or more of the individual columns—and especially with the overlaid injection technique disclosed in co-pending U.S. patent application Ser. No. 09/285,363 entitled "Rapid Characterization of Polymers", filed Apr. 2, 1999 by Petro et al. Referring again to FIG. 6, the suitability with overlaid injection is depicted as the dotted lines extending the chromatographic separation times for each of the samples, such that in any given column (e.g.,in Col. 1) the separation for a second sample (e.g., sample 5) is initiated while the separation of a first sample (e.g., sample 1) is completed. Overlaid detection is analogous (but not indicated in FIG. 6).

In an alternative approach, the sampling, injection and/or switching can be on an irregular time interval, and/or can occur in an irregular pattern. For example, in some applications in which a relatively long separation time is required, the auto-sampling robot can inject the sample of interest, and then be involved in other activities (e.g.,sample preparation, injection into other analytical systems, etc.). As another example, the timing of sample injection can be triggered by a control signal based on detection. In such a case, for example, if a first sample being characterized in a first column and twenty minutes are required to finish elution of all of the detectable components of the sample, then second through tenth samples (each requiring only 2 minutes to finish separation) can be characterized in the second, third and fourth columns, with the first column being reincorporated back into the pattern after it becomes available—with such availability being indicated, for example, based on a control signal from the first detector. This approach may be particularly preferred where the samples are very diverse and separation times are expected to vary substantially.

Chromatographic Channels

The number of parallel chromatographic channels, each comprising a one or more chromatography columns in series, can generally be two or more. The number of parallel chromatographic channels (and chromatography columns) is preferably 4 or more, 8 or more, 12 or more, 16 or more, 32 or more, 48 or more, 64 or more, or 96 or more. As discussed above in connection with FIG. 4C, nested multi-port switching valves can readily accommodate such large numbers of channels.

With reference to FIGS. 2A and 2B, the chromatographic channels can also include in-line filters 104a, 104b, 104c, 104d and/or pulse dampers (not shown)—typically incorporated into the sample supply conduits 80a, 80b, 80c, 80d. The in-line filters 104 can be of any suitable dimensions and mesh size. In one embodiment, effective for screening and evaluation of polymer samples, filters 104 can retain particles having a diameter of more than about 0.5 $\mu$m. In another embodiment for polymer samples, filters 104 can retain particles having a diameter of more than about 0.2 $\mu$m. Other sizes may also be employed, as suitable for a particular sample and/or process application. Additional in-line filters can likewise be employed. While shown in FIGS. 2A and 2B immediately downstream of the connectors 84a, 84b, 84c, 84d to the injection system 90, the particular location of the filters is not critical. Moreover, the sample could be filtered as a preparation step, prior to loading of the sample into the HPLC system. Other in-line systems, such as pulse-dampers can also be employed.

After injection of a sample into a stream of liquid serving as a mobile phase of a liquid chromatography channel, the sample is introduced into a chromatographic column containing a separation medium having a stationary-phase for separation of one or more components of the sample from other components thereof. Separation is effected by selectively eluting one or more of the components from the stationary-phase with the mobile-phase acting also as an eluant. The degree of separation, also referred to as the resolution of the sample components, can vary depending on the particular chemical nature of the sample components, and the quality of information required in the particular characterization application. In general, the separation performance in a given case can be controlled as a function of the column design/geometry, the stationary-phase media, and the elution conditions with the mobile phase.

The particular design of a chromatographic column for liquid chromatography is, in the general case, not narrowly critical. A number of columns known in the art can be employed in connection with the present invention—as purchased or with minor variations disclosed herein. In general, with reference to FIG. 2A, the chromatographic column 102 of a liquid chromatography system 10 comprises an interior surface defining a pressurizable separation cavity having a defined volume, an inlet port for receiving a mobile phase and for supplying a polymer sample to the separation cavity, and an effluent port for discharging the mobile phase and the polymer sample or separated components thereof from the separation cavity. The separation cavity is preferably pressurizable to pressures typically involved with high-pressure liquid chromatography—such pressures generally ranging from about atmospheric pressure to about 6000 psig (about 40 MPa). In some preferred liquid-chromatography characterization methods, discussed in greater detail below, the chromatographic column can be relatively shorter, and relatively wider, compared to traditional chromatographic separation columns. Such preferred high-aspect ratio columns are disclosed in greater detail in co-pending U.S. patent application Ser. No. 09/285,393 entitled "Rapic Characterization of Polymers", filed Apr. 2, 1999 by Petro et al.

The chromatographic column 102 (or a series of columns in one or more of the chromatographic channels) further comprises a separation medium having a stationaryphase within the separation cavity. The separation medium can consist essentially of a stationary-phase or can also include, in addition thereto, an inert support for the stationary phase. The column 102 can also comprise one or more fillers, flits (for separation medium retention and/or for filtering), and various fittings and features appropriate for preparing and/or maintaining the column for its intended application. The particular separation medium to be employed as the stationary-phase is not critical, and will typically depend on the separation strategy for the particular chemistry of the polymer samples of interest, as well as on the desired detection, sample-throughput and/or information quality. Typical stationary-phase media can be a bed of packed beads, fibers, irregular or other shaped-particles, or a monolithic medium (typically greater than about 5 mm in thickness), each of which can be characterized and optimized for a particular separation strategy with respect to the material, size, shape, pore size, pore size distribution, surface area, solvent regain, bed homogeneity (for packed shaped-particles), inertness, polarity, hydrophobicity, chemical stability, mechanical stability and solvent permeability, among other factors. Generally preferred stationary-phase include porous media (e.g., porous beads, porous monoliths), such as are suitable for gel permeation chromatography (GPC), precipitation-redissolution chromatography, normal-phase (e.g., adsorption) chromatography and reverse-phase chromatography, hydrophobic interaction chromatography, hydrophilic interaction chromatography, ion-exchange chromatography, affinity chromatography, among others. Non-porous particles or empty columns and/or capillaries with adsorptive walls can be used as well. If beads are employed, spherical beads are preferred over other shapes. Particularly preferred stationary-phase media for polymer characterization applications are disclosed in greater detail below, but can generally include silica, cross-linked polymeric resins (e.g. poly(2-3-dihydroxypropylmethacrylate), poly(hydroxyethyl methacrylate), and polystyrenic polymers such as poly (styrene-divinylbenzene)).

The mobile-phase fluid(s) employed to elute one or more polymer components from a chromatographic stationary-phase are not generally critical, and can vary depending on the chemistry of the separation being effected. The mobile phase can be varied with respect to composition, temperature, gradient rates, flow-rates, and other factors affecting selectivity, speed of separation, peak capacity (e.g., maximum number of components that can be separated with a single run) and/or resolution of a polymer component. Exemplary mobile-phase fluids for GPC include tetrahydrofuran (THF), toluene, dimethylformamide, water, aqueous buffers, trichlorobenzene and dichlorobenzene. Exemplary mobile-phase fluids for precipitation-redissolution chromatography include THF, methanol, hexane, acetone, acetonitrile and water. For adsorption chromatography, the mobile phase can include, for example, hexane, isooctane, decane, THF, dichloromethane, chloroform, diethylether and acetone. For reverse-phase chromatography, the mobile phase can include water, acetonitrile, methanol and THF, among others.

Significantly, preferred mobile phase flow are typically faster than flowrates employed conventionally for high-pressure liquid chromatography. The flowrates can vary, depending on the separation being effected, but can, in many instances, range from about 0.1 ml/min about 25 ml/min, and preferably range from about 1 ml/min to about 25 ml/min. It may be desirable, for some detector configurations, to split off a part of the sample-containing mobile phase such that the flow rate to a particular detector is reduced to an acceptable level. For liquid chromatography systems, such a split would typically occur after the column and before the detector.

Detection and Characterization

A sample such as a polymer sample is characterized by detecting a property of the sample, or by detecting a property of a component (e.g., a polymer component, a monomer component) of the sample. In many cases, the property is detected over a period of time, such that a variation in the property can be observed or detected or the rate of change of variation of a property can be observed or detected. In the general case, the detected property can be any property which can provide a scientifically meaningful basis of comparison between two different polymer samples or between two different polymer components—either directly, or after being correlated to a specific characterizing property of interest. The detected property can be a chemical property or a physical property of the sample or component thereof. In preferred applications, an optical property of the polymer sample or a component thereof can be detected. For example, an amount, frequency, intensity or direction of an incident light that is refracted, scattered, and/or absorbed by the polymer sample or a component thereof may be detected. Other properties, such as pressure or other factors affecting a particular characterizing property of interest (e.g., viscosity) can likewise be detected.

The detection step can be performed in parallel, in serial-parallel, or in series. With reference to FIGS. 2A and 2B, a property of a sample or of a component thereof, such as a chromatographically separated component thereof, can be detected with one or more detectors 130.

Parallel detection can be effected with two or more detectors (e.g. detectors 130a, 130b, 130c, 130d as shown in FIGS. 2A, 2B), and with each of such detectors being dedicated to one or more chromatographic channels (i.e., the flow cells of each of such detectors being in fluid communication with one or more chromatography columns). Parallel detection is particularly preferred in combination with rapid-serial techniques (e.g., overlaid injection/separation techniques) applied to any particular chromatographic channel. In one preferred particular approach, parallel flow cells—each being dedicated to one chromatographic channel—are employed, but the detection electronics associated therewith is electronically and serially switched between two or more of the flow cells, thereby reducing the amount of analysis circuitry required.

Figure 7:
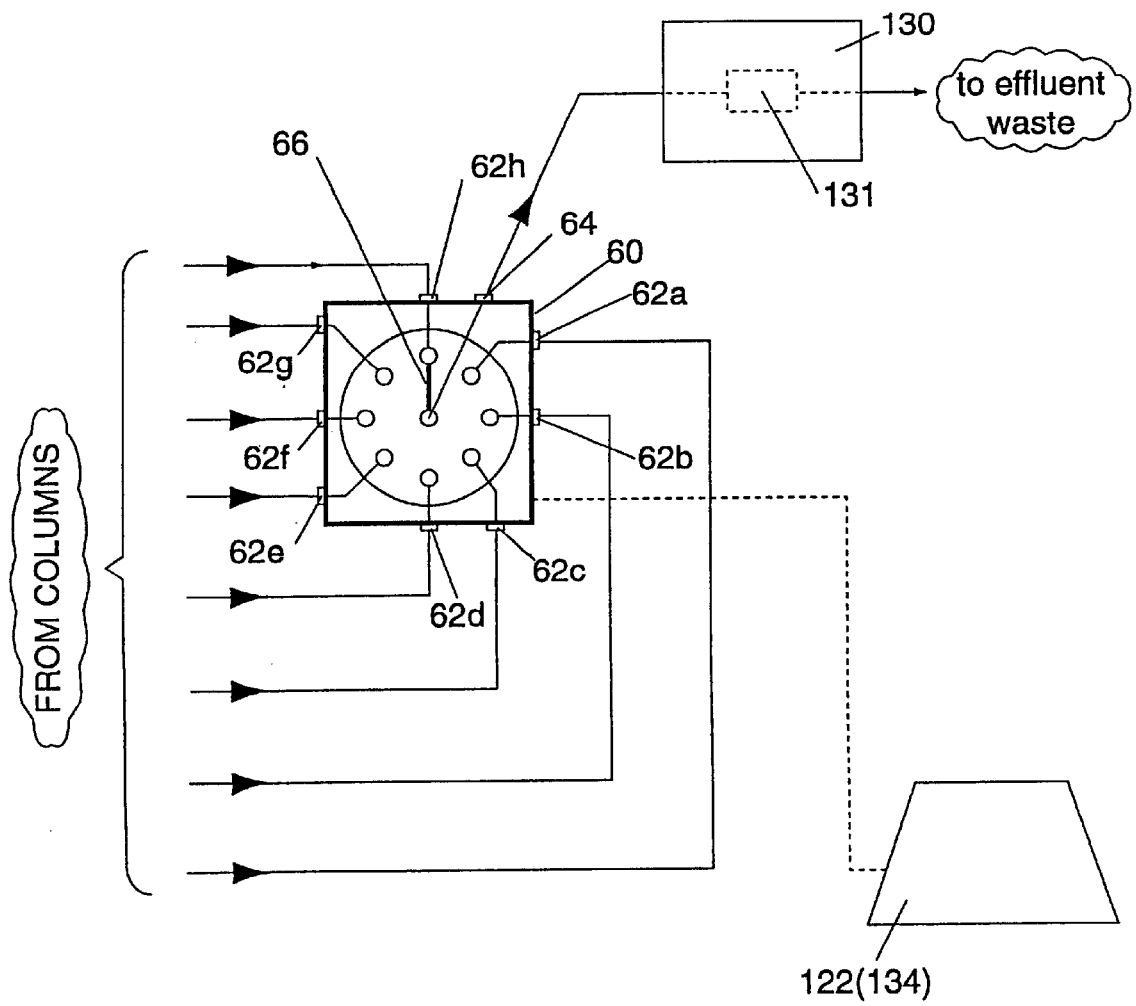
FIG. 7 is a schematic diagram illustrating a serial detection scheme that includes a detection switching valve and a flow cell detector.

Serial detection can also be effected, particularly where detection is faster than the separation, and within the timing intervals for sampling, injection and switching. In one serial embodiment, shown in FIG. 7, the parallel chromatography column eleuants (e.g.,mobile phase w/separated samples) can be serially directed through a detection switching valve 60 to the flow-cell 131 of a detector 130. The detection switching valve can be substantially the same as shown with respect to the sample multi-port switching valve 70. Briefly, the detection switching valve 60 will have two or more selectable inlet ports, 62a through 62h, and at least one outlet port 64. The inlet ports 62 are in fluid communication with two or more chromatography columns, and additionally, are selectable in fluid communication with the outlet ports 64. Switch 66 can be used to selectively connect one of the inlet ports 62 with the outlet port 64. The outlet port 64 is itself in fluid communication with the flow cell 131 of a detector 130. The switch 66 of the detection valve 60 can be manually or automatically actuated, and is preferably under microprocessor 122 (134) control. Referring briefly again to FIG. 6, serial detection is represented by detection boxes indicated with dashed lines.

In preferred embodiments, a property of a polymer sample or of a component thereof is detected with an optical detector such as a refractive-index detector, an ultraviolet-visual detector, a photodiode array detector, a static-light-scattering detector, a dynamic-light-scattering detector, and/or an evaporative-light-scattering detector—also known as an evaporative mass detector (EMD). Other detectors (e.g., a capillary viscometer detector, photodiode array detector (PDAD), infra-red detector, fluorescence detector, electro-chemical detector, conductivity detector, etc.) can likewise be employed in connection with the present invention. The particular nature of the detector (e.g., shape and/or configuration of a detection cavity 131 within the detector) is not generally critical.

In a preferred parallel detection protocol, the effluent streams from the parallel chromatographic columns are combined with another fluid stream comprising a treatment agent (e.g., a precipitation agent and/or derivatizing agent), such that at least one separated sample component of the injected samples are treated to change a property of at least one of the separated samples. Preferably, the sample components of the first and second (or more) samples are precipitated and/or derivatized—after separation but before detection—to make them more susceptible or to make them selectively detectable to detection, and most preferably, to optical detection. See European Patent EP 675 356 B1 and co-pending U.S. patent application, Ser. No. 09/670,503 entitled "Parallel High-Performance Liquid Chromatography With Post-Separation Treatment" filed Sep. 16, 2000 by Petro et al., which claims the priority benefit of Ser. No. 60/157,338, entitled "Parallel High-Performance Liquid Chromatography with Post-Separation Treatment", filed Oct. 1, 1999, each of which is incorporated by reference in its entirety for all purposes. Advantageously, such protocols can be cost-effectively applied in combination with parallel optical detectors, and moreover, such combination can be efficiently and suitable applied in mini- and micro-scaled liquid chromatography systems. As noted below, such mini- and micro-scale liquid chromatography systems can be advantageously applied in connection with combinatorial chemistry and materials science research.

The protocols for characterizing one or more samples preferably further comprise determining a property of interest from the detected property. The physically-detected properties, such as the capability of the sample or component thereof to refract, scatter, emit or absorb light can be correlated to properties of interest. For polymer samples, for example, such properties of interest include, without limitation, weight-average molecular weight, number-average molecular weight, viscosity-average molecular weight, peak molecular weight, approximate molecular weight, polydispersity index, molecular-weight-distribution shape, relative or absolute component concentration, chemical composition, conversion, concentration, mass, hydrodynamic radius ($R_h$), radius of gyration ($R_g$), chemical composition, amounts of residual monomer, presence and amounts of other low-molecular weight impurities in polymer samples, particle or molecular size, intrinsic viscosity, molecular shape, molecular conformation, and/or agglomeration or assemblage of molecules. The correlation between a detected property and a determined property of interest can be based on mathematical models and/or empirical calibrations. Such correlation methods are generally known in the art, and are typically incorporated into commercially-available chromatographic detectors and/or detector or data-acquisition software.

For combinatorial polymer science research applications, as well as other applications, the characterization protocols can be effected to determine at least a weight-average molecular weight as a characterization property of primary importance. Other characterization properties of interest of substantial importance, include number-average molecular weight, polydispersity index, and molecular-weight-distribution shape. For polymer samples that are polymerization product mixtures, another characterization property of substantial importance is conversion data for the polymerization reaction, typically expressed as % monomer converted into polymer. The composition of the polymer sample or of particular components thereof (e.g. polymer components) can also be of substantial importance.

For determining weight-average molecular weight from detected properties, a liquid chromatography system or a flow-injection analysis system can advantageously employ a single detector or a combination of two or more detectors. In a single-detector embodiment, for example, a dynamic light-scattering (DLS) detector can be used by itself to determine an average hydrodynamic radius or a distribution of hydrodynamic radii from the detected scattered light. The hydrodynamic radii can, in turn, be correlated to an average molecular weight or a molecular weight distribution. In a two-detector embodiment, for example, a static-light scattering (SLS) detector (where the detected scattered light is a function of weight-average molecular weight ($M_W$), concentration (C) and the square of the refractive index increment, $(dn/dC)^2$) can be combined with a refractive index (RI) detector (where the detected refracted light is a function of (C) and (dn/dC)), with an ultraviolet/visible light absorbance (UV/VIS) detector (where the detected absorbed light is a function of (C)), or with an evaporative light scattering detector (ELSD) (where the detected scattered light is a function of (C)). In another embodiment, a single-detector or multiple detectors (e.g., SLS) can detect the intensity of light scattered by the sample or sample component at two or more different angles, which can be correlated to molecular weight.

For polymer samples that are polymerization product mixtures, conversion data for the polymerization reaction of which the sample is representative can be determined by chromatographically resolving the polymer component(s) and monomer component(s), determining a molecular-weight distribution for such components, integrating areas under the respective peaks, and then comparing the integrated peak areas (e.g., using response factors for particular components and detector employed). Another approach for calculating conversion involves converting the polymer-peak area into polymer concentration or mass using a concentration-detector response calibration plot, and then comparing the portion of the polymer mass or concentration found in the sample to the expected mass or concentration assuming 100% stoichiometric conversion. Composition data for a polymer sample can be determined from the consumption of monomer or comonomers or, alternatively, from a retention time per volume of the polymer peak or a fraction thereof.

Advantageously, an ELSD detector, or other detectors that are not particularly sensitive to low-molecular weight components of a polymer sample, can be advantageously employed in connection with the flow characterization protocols of the invention to achieve a high sample-throughput. As discussed in greater detail below, detectors that are insensitive to low-molecular weight components can be advantageously employed in connection with rapid-serial overlapping techniques. Moreover, because the ELSD is also less sensitive to temperature variations than other types of mass detectors (eg., RI detector) and is not required to be in thermal equilibrium with the sample being detected, an ELSD detector can be employed advantageously in connection with high-temperature polymer characterization systems. Hence, detecting a property of a polymer sample or a component there of with an ELSD or with other low-MW insensitive or less temperature sensitive mass detectors provides a further aspect for improving the sample throughput—particularly for a liquid chromatography system 10.

The aforementioned characterizing properties of interest can, once determined, be mathematically combined in various combinations to provide figures of merit for various properties or attributes of interest. In particular, for example, molecular weight, conversion and polydispersity index can be evaluated versus polymerization process time to provide mechanistic insights as to how polymers are formed. Other combinations of the fundamental characterization properties of interest will be apparent to those of skill in the art.

Specific applications and/or combinations of detectors, as well as correlation protocols, are discussed in greater detail in the above-identified co-pending U.S. applications to which the present application claims priority.

Microprocessors

Referring to FIG. 2A, FIG. 2B, FIG. 4A, FIG. 5 and FIG. 7, one or more microprocessors can, as noted above, be employed for controlling every aspect of the HPLC systems, including: the pump 116 (e.g., mobile-phase flow-rate, flowrate gradients, compositional gradients, temperature gradients, acceleration rates for such gradients); the reservoir 114 (e.g., temperature, level); the auto-sampler 200 (e.g., movements between spatial position, timing thereof, sample selection, sample preparation, sampling pump flow-rates, and other operations), the injection valve 100 (e.g., timing, selection of sample loops, etc.); the multi-port switching valve 70, the column 102 (eg., column selection (if multiple columns and automated column-switching valves are present), column temperature); the detection switch 60 (as applicable), the detector 130 (e.g., data acquisition (e.g., sampling rate), data processing (e.g., correlation)); the detector parameters (e.g., wavelength); and/or overall system conditions (e.g., system pressure, temperature). Software is typically available from detector and/or liquid chromatography system manufacturers (e.g. MILLENNIUM™ 2000 software available from Waters (Milford, Mass.)).

Inverse Chromatography and Other Solid-Phase Interaction Evaluations

In one application, the present invention can be employed, substantially as described above, for "inverse chromatography" studies, in which the object and subject of the study are reversed as compared to "regular" chromatography. In addition, this concept can be advantageously extended to the study of other solid phase—liquid phase interactions (that may not necessarily involve separation of sample components and, as such, may not be considered to be "chromatography").

In general, a plurality of samples are serially injected into a mobile phase supplied in parallel to two or more columns, where the columns comprise solid or supported materials. The solid or supported materials can be separation media, or can be other types of solids for which there is an interest to study interactions with dissolved, dispersed or emulsified samples in a mobile phase and/or vice versa. The interactions between the injected samples, or one or more components of the injected samples, and the solid or supported materials in the columns is then evaluated.

Samples

In general, the sample materials can generally comprise elements or compounds selected from the group consisting of organic materials, inorganic materials and metal-ligands. In some applications, the candidate materials will consist essentially of organic materials, consist essentially of inorganic materials, or consist essentially of metal-ligand materials. Moreover, in some applications, the sample materials will be compositions comprising mixtures of organic materials, inorganic materials and/or metal-ligand materials in the various possible combinations.

Organic materials are considered to include compounds having covalent carbon-carbon bonds. In some embodiments, the organic materials are preferably organic polymers, small-organic molecules having a molecular weight of less than about 1000, or non-biological molecules. Non-biological organic materials include organic materials other than biological materials. Biological materials are considered to include nucleic acid polymers (e.g., DNA, RNA) amino acid polymers (e.g., enzymes) and small organic compounds (e.g., steroids, hormones) where the small organic compounds have biological activity, especially biological activity for humans or commercially significant animals such as pets and livestock, and where the small organic compounds are used primarily for therapeutic or diagnostic purposes. Although in some applications the sample materials being characterized by the HPLC system are preferably not, themselves, biological organic materials, the sample materials of the invention (e.g. polymers) can be employed to prepare or separate biological organic materials. Polymeric sample materials are discussed in greater detail below.

Inorganic materials include elements (including carbon in its atomic or molecular forms), compounds that do not include covalent carbon-carbon bonds (but which could include carbon covalently bonded to other elements, e.g., $CO_2$), and compositions including elements and/or such compounds.

The samples can comprise materials that are an element, a compound or a composition comprising a plurality of elements and/or compounds. The sample materials are generally in a liquid state or are capable of being dissolved, dispersed or emulsified in a liquid phase, as appropriate for chromatographic separation (or, with respect to inverse chromatagraphy, as appropriate for the interaction between the samples and the solid or supported material).

The samples can be reaction products from a chemical reaction, which for purposes hereof, means a process in which at least one covalent bond of a molecule or compound is formed or broken. As such, immunoreactions in which immunoaffinity is based solely on hydrogen bonding or other forces—while chemical processes—are not considered to be chemical reactions. Reactions that include activation of, breaking and/or formation of H—Si, H—H, H—N, H—O, H—P, H—S, C—H, C—C, C=C, C≡C, C-halogen, C—N, C—O, C—S, C—P, C—B and C—Si bonds are exemplary. More specific exemplary chemical reactions from which reaction-product samples may derive, include, without limitation, oxidation, reduction, hydrogenation, dehydrogenation (including transfer hydrogenation), hydration, dehydration, hydrosilylation, hydrocyanation, hydroformylation (including reductive hydroformylation), carbonylation, hydrocarbonylation, amidocarbonylation, hydrocarboxylation, hydroesterification, hydroamination, hetero-cross-coupling reaction, isomerization (including carbon-carbon double bond isomerization), dimerization, trimerization, polymerization, co-oligomerization (e.g. CO/alkene, CO/alkyne), co-polymerization (e.g., CO/alkene, CO/alkyne), insertion reaction, aziridation, metathesis (including olefin metathesis), carbon-hydrogen activation, cross coupling, Friedel-Crafts acylation and alkylation, Diels-Alder reactions, C-C coupling, Heck reactions, arylations, Fries rearrangement, vinylation, acetoxylation, aldol-type condensations, aminations, reductive aminations, epoxidations, hydrodechlorinations, hydrodesulfurations and Fischer-Tropsch reactions, asymmetric versions of any of the aforementioned reactions, and combinations of any of the aforementioned reactions in a complex reaction sequence of consecutive reactions. A combinatorial library or array comprising different reaction-product samples can be formed, for example, as the reaction product from a chemical reactions involving a library of diverse catalysts, and/or variations in reactants, co-reactants, cataloreactants, selective blocking moieties, etc. As used herein, the term catalyst is intended to include a material that enhances the reaction rate of a chemical reaction of interest or that allows a chemical reaction of interest to proceed where such reaction would not substantially proceed in the absence of the catalyst.

Polymer Samples

The present invention is particularly preferred in connection with the characterization of polymer samples, and especially, combinatorial libraries comprising different polymer samples. The polymer sample can be a homogeneous polymer sample or a heterogeneous polymer sample, and in either case, comprises one or more polymer components. As used herein, the term "polymer component" refers to a sample component that includes one or more polymer molecules. The polymer molecules in a particular polymer component have the same repeat unit, and can be structurally identical to each other or structurally different from each other. For example, a polymer component may comprise a number of different molecules, with each molecule having the same repeat unit, but with a number of molecules having different molecular weights from each other (e.g., due to a different degree of polymerization). As another example, a heterogeneous mixture of copolymer molecules may, in some cases, be included within a single polymer component (e.g., a copolymer with a regularly-occurring repeat unit), or may, in other cases, define two or more different polymer components (e.g., a copolymer with irregularly-occurring or randomly-occurring repeat units). Hence, different polymer components include polymer molecules having different repeat units. It is possible that a particular polymer sample (e.g., a member of a library) will not contain a particular polymer molecule or polymer component of interest.

The polymer molecule of the polymer component is preferably a non-biological polymer. A non-biological polymer is, for purposes herein, a polymer other than an amino-acid polymer (e.g., protein) or a nucleic acid polymer (e.g. deoxyribonucleic acid (DNA)). The non-biological polymer molecule of the polymer component is, however, not generally critical; that is, the systems and methods disclosed herein will have broad application with respect to the type (e.g., architecture, composition, synthesis method or mechanism) and/or nature (e.g., physical state, form, attributes) of the non-biological polymer. Hence, the polymer molecule can be, with respect to homopolymer or copolymer architecture, a linear polymer, a branched polymer (e.g. short-chain branched, long-chained branched, hyper-branched), a cross-linked polymer, a cyclic polymer or a dendritic polymer. A copolymer molecule can be a random copolymer molecule, a block copolymer molecule (e.g., di-block, tri-block, multi-block, taper-block), a graft copolymer molecule or a comb copolymer molecule. The particular composition of the non-biological polymer molecule is not critical, and can include repeat units or random occurrences of one or more of the following, without limitation: polyethylene, polypropylene, polystyrene, polyolefin, polyimide, polyisobutylene, polyacrylonitrile, poly(vinyl chloride), poly(methyl methacrylate), poly(vinyl acetate), poly(vinylidene chloride), polytetrafluoroethylene, polyisoprene, polyacrylamide, polyacrylic acid, polyacrylate, poly(ethylene oxide), poly(ethyleneirnine), polyamide, polyester, polyurethane, polysiloxane, polyether, polyphosphazine, polymethacrylate, and polyacetals. Polysaccharides are also preferably included within the scope of non-biological polymers. While some polysaccharides are of biological significance, many polysaccharides, and particularly semi-synthetic polysaccharides have substantial industrial utility with little, if any biological significance. Exemplary naturally-occurring polysaccharides include cellulose, dextran, gums (e.g., guar gum, locust bean gum, tamarind xyloglucan, pullulan), and other naturally-occurring biomass. Exemplary semi-synthetic polysaccharides having industrial applications include cellulose diacetate, cellulose triacetate, acylated cellulose, carboxymethyl cellulose and hydroxypropyl cellulose. In any case, such naturally-occurring and semi-synthetic polysaccharides can be modified by reactions such as hydrolysis, esterification, alkylation, or by other reactions.

In typical applications, a polymer sample is a heterogeneous sample comprising one or more polymer components, one or more monomer components and/or a continuous fluid phase. In copolymer applications, the polymer sample can comprise one or more copolymers, a first comonomer, a second comonomer, additional comonomers, and/or a continuous fluid phase. The polymer samples can, in any case, also include other components, such as catalysts, catalyst precursors (e.g. ligands, metal-precursors), solvents, initiators, additives, products of undesired side-reactions (e.g., polymer gel, or undesired homopolymer or copolymers) and/or impurities. Typical additives include, for example, surfactants, control agents, plasticizers, cosolvents and/or accelerators, among others. The various components of the heterogeneous polymer sample can be uniformly or non-uniformly dispersed in the continuous fluid phase.

The polymer sample is preferably a liquid polymer sample, such as a polymer solution, a polymer emulsion, a polymer dispersion or a polymer that is liquid in the pure state (i.e., a neat polymer). A polymer solution comprises one or more polymer components dissolved in a solvent. The polymer solution can be of a form that includes well-dissolved chains and/or dissolved aggregated micelles. The solvent can vary, depending on the application, for example with respect to polarity, volatility, stability, and/or inertness or reactivity. Typical solvents include, for example, tetrahydrofuran (THF), toluene, hexane, ethers, trichlorobenzene, dichlorobenzene, dimethylformamide, water, aqueous buffers, alcohols, etc. According to traditional chemistry conventions, a polymer emulsion can be considered to comprise one or more liquid-phase polymer components emulsified (uniformly or non-uniformly) in a liquid continuous phase, and a polymer dispersion can be considered to comprise solid particles of one or more polymer components dispersed (uniformly or non-uniformly) in a liquid continuous phase. The polymer emulsion and the polymer dispersion can also be considered, however, to have the more typically employed meanings specific to the art of polymer science—of being a emulsion-polymerization product and dispersion-polymerization product, respectively. In such cases, for example, the emulsion polymer sample can more generally include one or more polymer components that are insoluble, but uniformly dispersed, in a continuous phase, with typical emulsions including polymer component particles ranging in diameter from about 2 nm to about 500 nm, more typically from about 20 nm to about 400 nm, and even more typically from about 40 nm to about 200 nm. The dispersion polymer sample can, in such cases, generally include polymer component particles that are dispersed (uniformly or nonuniformly) in a continuous phase, with typical particles having a diameter ranging from about 0.2 $\mu$m to about 1000 $\mu$m, more typically from about 0.4 $\mu$m to about 500 $\mu$m, and even more typically from about 0.5 $\mu$m to about 200 $\mu$m. Exemplary polymers that can be in the form of neat polymer samples include dendrimers, and siloxane, among others. The liquid polymer sample can also be employed in the form of a slurry, a latex, a microgel a physical gel, or in any other form sufficiently tractable for analysis as described and claimed herein. Liquid samples are useful in the automated sample-handling tools that prepare and automatically sample each member of a polymer library. Liquid samples also allow the sample to flow in the chromatographic system or characterization system. In some cases, polymer synthesis reactions (i.e., polymerizations) directly produce liquid samples. These may be bulk liquid polymers, polymer solutions, or heterogeneous liquid samples such as polymer emulsions, latices, or dispersions. In other cases, the polymer may be synthesized, stored or otherwise available for characterization in a non-liquid physical state, such as a solid state (e.g., crystalline, semi-crystalline or amorphous), a glassy state or rubbery state. Hence, the polymer sample may need to be dissolved, dispersed or emulsified to form a liquid sample by addition of a continuous liquid-phase such as a solvent. The polymer sample can, regardless of its particular form, have various attributes, including variations with respect to polarity, solubility and/or miscibility.

In preferred applications, the polymer sample is a polymerization product mixture. As used herein, the term "polymerization product mixture" refers to a mixture of sample components obtained as a product from a polymerization reaction. An exemplary polymerization product mixture can be a sample from a combinatorial library prepared by polymerization reactions, or can be a polymer sample drawn off of an industrial process line. In general, the polymer sample may be obtained after the synthesis reaction is stopped or completed or during the course of the polymerization reaction. Alternatively, samples of each polymerization reaction can be taken and placed into an intermediate array of vessels at various times during the course of the synthesis, optionally with addition of more solvent or other reagents to arrest the synthesis reaction or prepare the samples for analysis. These intermediate arrays can then be characterized at any time without interrupting the synthesis reaction. It is also possible to use polymer samples or libraries of polymer samples that were prepared previously and stored. Typically, polymer libraries can be stored with agents to ensure polymer integrity. Such storage agents include, for example, antioxidants or other agents effective for preventing cross-linking of polymer molecules during storage. Depending upon the polymerization reaction, other processing steps may also be desired, all of which are preferably automated. The polymerization scheme and/or mechanism by which the polymer molecules of the polymer component of the sample are prepared is not critical, and can include, for example, reactions considered to be addition polymerization, condensation polymerization, step-growth polymerization, and/or chain-growth polymerization reactions. Viewed from another aspect, the polymerization reaction can be an emulsion polymerization or a dispersion polymerization reaction. Viewed more specifically with respect to the mechanism, the polymerization reaction can be radical polymerization, ionic polymerization (e.g., cationic polymerization, anionic polymerization), and/or ring-opening polymerization reactions, among others. Non-limiting examples of the foregoing include, Ziegler-Natta or Kaminsky-Sinn reactions and various copolymerization reactions. Polymerization product mixtures can also be prepared by modification of a polymeric starting materials, by grafting reactions, chain extension, chain scission, functional group interconversion, or other reactions.

The sample size is not narrowly critical, and can generally vary, depending on the particular characterization protocols and systems used to characterize the sample or components thereof. Typical sample sizes can range from about 0.1 μl to about 1 ml, more typically from about 1 μl to about 1000 μl, even more typically from about 5 μl to about 100 μl, and still more typically from about 10 μl to about 50 μl. A generally preferred sample size for flow characterization systems and, particularly for liquid chromatography, is a sample size of about 20 μl.

The polymer sample, such as a polymerization product mixture, can be a raw, untreated polymer sample or can be pretreated in preparation for characterization. Typical sample preparation steps include preliminary, non-chromatographic separation of one or more components of a polymer sample from other components, dilution, mixing and/or redissolution (e.g., from a solid state), among other operations. Preliminary separation methods can help remove large-scale impurities such as dust, coagulum or other impurities. Such separation methods can include, for example: filtering (e.g. with a microfilter having pore sizes that allow the passage of particles less than about 0.5 μm or 0.2 μm); precipitation of polymer components, monomer components and/or other small-molecule components, decanting, washing, scavenging (e.g., with drying agents), membrane separation (e.g., diafiltration, dialysis), evaporation of volatile components and/or ion-exchange. The sample is preferably diluted, if necessary, to a concentration range suitable for detection. For typical liquid chromatography applications, for example, the sample concentration prior to loading into the liquid chromatography system can range from about 0.01 mg/ml to a neat sample, more typically from about 0.01 mg/ml to about 100 mg/ml, and even more typically from about 0.1 mg/ml to about 50 mg/ml. More specific concentration ranges typical for liquid chromatography samples include from about 0.1 mg/ml to about 20 mg/ml, and from about 0.5 mg/ml to about 5 mg/ml. For flow-injection analysis systems, in which the sample is detected without substantial chromatographic separation thereof, much more dilute solutions can be employed. Hence, the concentration can range from a detectable concentration level (for the particular detector employed) up to about 1 mg/ml, or more in some applications. Typical concentrations can be about $1\times10^{-2}$ wt %, about $\times10^{-1}$ wt % or about $1\times10^{-4}$ wt %. Mixing can be required to increase the uniformity of a polymer sample emulsion or dispersion, and/or to integrate one or more additional components into the polymer sample. Preparation steps, and particularly rapid preparation techniques, can be an important aspect for combinatorial polymer investigations—since polymer samples may be synthesized in a form not ideally suited for immediate characterization.

Although the primary applications of the present invention are directed to combinatorial polymer science research and/or quality control for industrial polymer synthesis or processing protocols, aspects of the invention can have applications involving non-polymer samples. A non-polymer sample can be a material that comprises an organic or an inorganic non-polymer element or compound. Oligomers are considered to be polymers rather than non-polymers. The non-polymer molecule is, in some cases, preferably a non-biological non-polymer element or compound. Such non-biological non-polymer elements or compounds include non-polymer elements or compounds other than those having a well-characterized biological activity and/or a primary commercial application for abiological field (e.g., steroids, hormones, etc.). More particularly, such non-biological, non-polymer elements or compounds can include organic or inorganic materials such as pigments, carbon powders (e.g., carbon black), metals, metal oxides, metal salts, metal colloids, metal ligands, etc., without particular limitation.

Pluralities of Samples/Libraries of Samples

A plurality of samples such as polymer samples comprises 2 or more samples that are physically or temporally separated from each other—for example, by residing in different sample containers, by having a membrane or other partitioning material positioned between samples, by being partitioned (e.g., in-line) with an intervening fluid, by being temporally separated in a flow process line (e.g. as sampled for process control purposes), or otherwise. The plurality of samples preferably comprises 4 or more samples, more preferably 8 or more samples, and even more preferably 10 or more samples. Four samples can be employed, for example, in connection with experiments having one control sample and three polymer samples varying (e.g. with respect to composition or process conditions as discussed above) to be representative of a high, a medium and a low-value of the varied factor—and thereby, to provide some indication as to trends. Eight samples can provide for additional variations in the explored factor space. Moreover, eight samples corresponds to the number of parallel polymerization reactors in the PPR-8™, being selectively offered as one of the Discovery Tools™ of Symyx Technologies, Inc. (Santa Clara, Calif.). Higher numbers of samples can be investigated, according to the methods of the invention, to provide additional insights into larger compositional and/or process space. In some cases, for example, the plurality of samples can be 15 or more samples, preferably 20 or more samples, more preferably 40 or more samples and even more preferably 80 or more samples. Such numbers can be loosely associated with standard configurations of parallel reactor configurations (e.g. the PPR-48™, Symyx Technologies, Inc.) and/or of standard sample containers (e.g. 96-well microtiter plate-type formats). Moreover, even larger numbers of samples such as polymer samples can be characterized according to the methods of the present invention for larger scale research endeavors. Hence, the number of samples can be 150 or more, 400 or more, 500 or more, 750 or more, 1,000 or more, 1,500 or more, 2,000 or more, 5,000 or more and 10,000 or more polymer samples. As such, the number of samples can range from about 2 samples to about 10,000 samples, and preferably from about 8 samples to about 10,000 samples. In many applications, however, the number of samples can range from about 80 samples to about 1500 samples. In some cases, in which processing of samples using typical 96-well microtiter-plate formatting is convenient or otherwise desirable, the number of samples can be 96*N, where N is an integer ranging from about 1 to about 100. For many applications, N can suitably range from 1 to about 20, and in some cases, from 1 to about 5.

The plurality of samples can be a combinatorial library of samples. A library of samples comprises of two or more different samples, and can be in an array format as spatially separated samples—preferably on a common substrate, or temporally separated—for example, in a flow system. Candidate samples (ie., members) within a library may differ in a definable and typically predefined way, including with regard to chemical structure, processing (e.g., synthesis) history, mixtures of interacting components, purity, etc. The samples can be spatially separated, preferably at an exposed surface of the substrate, such that the array of samples are separately addressable for sampling into the characterization system and subsequent characterization thereof The two or more different samples can reside in sample containers formed as wells in a surface of the substrate. The number of samples included within the library can generally be the same as the number of samples included within the plurality of samples, as discussed above. In general, however, not all of the samples within a library of samples need to be different samples. When process conditions are to be evaluated, the libraries may contain only one type of sample. Typically, however, for combinatorial polymer science research applications, at least two or more, preferably at least four or more, even more preferably eight or more and, in many cases most, and allowably each of the plurality of polymer samples in a given library of polymer samples will be different from each other. Specifically, a different polymer sample can be included within at least about 50%, preferably at least 75%, preferably at least 80%, even more preferably at least 90%, still more preferably at least 95%, yet more preferably at least 98% and most preferably at least 99% of the polymer samples included in the sample library. In some cases, all of the polymer samples in a library of polymer samples will be different from each other.

The substrate can be a structure having a rigid or semi-rigid surface on which or into which the array of polymer samples can be formed or deposited. The substrate can be of any suitable material, and preferably consists essentially of materials that are inert with respect to the polymer samples of interest. Certain materials will, therefore, be less desirably employed as a substrate material for certain polymerization reaction process conditions (e.g., high temperatures—especially temperatures greater than about 100° C.—or high pressures) and/or for certain reaction mechanisms. Stainless steel, silicon, including polycrystalline silicon, single-crystal silicon, sputtered silicon, and silica ($SiO_2$) in any of its forms (quartz, glass, etc.) are preferred substrate materials. Other known materials (e.g., silicon nitride, silicon carbide, metal oxides (eg., alumina), mixed metal oxides, metal halides (e.g., magnesium chloride), minerals, zeolites, and ceramics) may also be suitable for a substrate material in some applications. Organic and inorganic polymers may also be suitably employed in some applications of the invention. Exemplary polymeric materials that can be suitable as a substrate material in particular applications include polyimides such as Kapton™, polypropylene, polytetrafluoroethylene (PTFE) and/or polyether etherketone (PEEK), among others. The substrate material is also preferably selected for suitability in connection with known fabrication techniques. As to form, the sample containers formed in, at or on a substrate can be preferably, but are not necessarily, arranged in a substantially flat, substantially planar surface of the substrate. The sample containers can be formed in a surface of the substrate as dimples, wells, raised regions, trenches, or the like. Non-conventional substrate-based sample containers, such as relatively flat surfaces having surface-modified regions (e.g., selectively wettable regions) can also be employed. The overall size and/or shape of the substrate is not limiting to the invention. The size and shape can be chosen, however, to be compatible with commercial availability, existing fabrication techniques, and/or with known or later-developed automation techniques, including automated sampling and automated substrate-handling devices. The substrate is also preferably sized to be portable by humans. The substrate can be thermally insulated, particularly for high-temperature and/or low-temperature applications. In preferred embodiments, the substrate is designed such that the individually addressable regions of the substrate can act as polymerization reaction vessels for preparing a polymerization product mixture (as well as sample containers for the two or more different polymer samples during subsequent characterization thereof. Glass-lined, 96-well, 384-well and 1536-well microtiter-type plates, fabricated from stainless steel and/or aluminum, are preferred substrates for a library of polymer samples. The choice of an appropriate specific substrate material and/or form for certain applications will be apparent to those of skill in the art in view of the guidance provided herein.

The library of polymer materials can be a combinatorial library of reaction product mixtures such as polymerization product mixtures. Polymer libraries can comprise, for example, polymerization product mixtures resulting from polymerization reactions that are varied with respect to, for example, reactant materials (e.g. monomers, comonomers), catalysts, catalyst precursors, initiators, additives, the relative amounts of such components, reaction conditions (e.g., temperature, pressure, reaction time) or any other factor affecting polymerization. Design variables for polymerization reactions are well known in the art. See generally, Odian, *Principles of Polymerization*, 3$^{rd}$ Ed., John Wiley & Sons, Inc. (1991). A library of polymer samples may be prepared in arrays, in parallel polymerization reactors or in a serial fashion. Exemplary methods and apparatus for preparing polymer libraries—based on combinatorial polymer synthesis approaches—are disclosed in co-pending U.S. patent application Ser. No. 09/211,982 of Turner et al. filed Dec. 14, 1998, co-pending U.S. patent application Ser. No. 09/227,558 of Turner et al. filed Jan. 8, 1999, co-pending U.S. patent application Ser. No. 09/235,368 of Weinberg et al. filed Jan. 21, 1999, and co-pending U.S. provisional patent application Ser. No. 60/122,704 entitled "Controlled, Stable Free Radical Emulsion and Water-Based Polymerizations", filed Mar. 9, 1999 by Klaerner et al. See also, PCT Patent Application WO 96/11878.

The libraries can be advantageously characterized directly, without being isolated, from the reaction vessel in which the polymer was synthesized. Thus, reagents, catalysts or initiators and other additives for making polymers may be included with the polymer sample for characterization or screening.

While such methods are preferred for a combinatorial approach to polymer science research, they are to be considered exemplary and non-limiting. As noted above, the particular polymer samples characterized according to the methods and with the apparatus disclosed herein can be from any source, including, but not limited to polymerization product mixtures resulting from combinatorially synthesis approaches.

Mini- and Micro-Scale Applications

The methods of the present invention can be applied in connection with "normal" scale HPLC systems, and can also be applied to smaller scale systems—including particularly mini-scale systems and micro-scale systems. As used herein, mini-scale systems are considered to include those having mobile-phase supply conduits and/or separation units (e.g., chromatographic columns) with a diameter ranging from about 3 mm to about 500 $\mu$m and micro-scale systems are considered to include those having mobile-phase supply conduits with a diameter of about 500 $\mu$m or less. For other than circular cross-sections, equivalent dimensions can be determined based on hydraulic radius.

In light of the detailed description of the invention presented above, it can be appreciated that the several objects of the invention are achieved. The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention.

I claim:

1. A liquid chromatography system useful for rapid separation or characterization of a plurality of samples, the system comprising two or more chromatographic columns, two or more supply conduits providing continuous parallel fluid communication between a liquid mobile-phase source and the two or more chromatographic columns, respectively, the fluid communication being provided by each of the two or more supply conduits through one or more flow restrictors, an injection system, comprising an injector and a multi-port switching valve, for serially and distributively injecting a plurality of samples into a liquid mobile phase supplied in parallel to the two or more chromatographic columns, the injector having a sample-loading port for serially receiving a plurality of samples and having a sample-discharge port for discharging the plurality of samples under pressure to the switching valve, the switching valve having an inlet port and two or more selectable outlet ports, the inlet port being in fluid communication with the sample-discharge port of the injector and being in selectable fluid communication with the two or more selectable outlet ports, the two or more selectable outlet ports being in fluid communication with the two or more chromatographic columns, respectively, such that the plurality of samples can be serially and distributively injected into the mobile phase of the two or more chromatographic columns.

2. The liquid chromatography system of claim 1 further comprising a control system for controlling which of the two or more selectable outlet ports of the switching valve is in fluid communication with the inlet port of the switching valve.

3. The liquid chromatography system of claim 1 wherein the two or more chromatographic columns are four or more chromatographic columns, the two or more mobile phase supply conduits are four or more mobile phase supply conduits, the switching valve has four or more selectable outlet ports, the inlet port is in selectable fluid communication with the four or more selectable outlet ports, and the four or more selectable outlet ports are in fluid communication with the four or more chromatographic columns, respectively, such that the plurality of samples can be serially and distributively injected into the mobile phase of the four or more chromatographic columns.

4. The liquid chromatography system of claim 1 wherein the injector is a multi-loop injection valve.

5. The liquid chromatography system of claim 1 further comprising one or more detectors in fluid communication with the two or more chromatographic columns.

6. A system for evaluating interactions between a plurality of liquid samples and one or more solid or supported materials, the system comprising two or more columns comprising solid or supported materials, two or more supply conduits providing continuous parallel fluid communication between a liquid mobile-phase source and the two or more columns, respectively, the fluid communication being provided by each of the two or more supply conduits through one or more flow restrictors, and an injection system, comprising an injector and a multi-port switching valve, for serially and distributively injecting a plurality of liquid samples into a liquid mobile phase supplied to the two or more columns, the injector having a sample-loading port for serially receiving the plurality of samples and having a sample-discharge port for discharging the plurality of samples under pressure to the switching valve, the switching valve having an inlet port and two or more selectable outlet ports, the inlet port being in fluid communication with the sample-discharge port of the injector and being in selectable fluid communication with the two or more selectable outlet ports, the two or more selectable outlet ports being in fluid communication with the two or more columns, respectively, such that the plurality of samples can be serially and distributively injected into the mobile phase of the two or more columns.

* * * * *